United States Patent
Li et al.

(10) Patent No.: US 7,238,792 B2
(45) Date of Patent: Jul. 3, 2007

(54) FOLDABLE POLYMERS AS PROBES

(75) Inventors: Alexander D. Q. Li, Pullman, WA (US); Wei Wang, Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 299 days.

(21) Appl. No.: 10/803,564

(22) Filed: Mar. 17, 2004

(65) Prior Publication Data

US 2004/0224372 A1 Nov. 11, 2004

Related U.S. Application Data

(60) Provisional application No. 60/455,700, filed on Mar. 18, 2003.

(51) Int. Cl.
*C07H 19/00* (2006.01)
*C07H 21/02* (2006.01)
*C07H 21/04* (2006.01)
*C12Q 1/68* (2006.01)
*G01N 33/53* (2006.01)

(52) U.S. Cl. ............... 536/22.1; 536/23.1; 536/24.3; 435/6; 435/7.1

(58) Field of Classification Search ............ 435/6, 435/7.1; 536/23.1, 24.3, 22.1
See application file for complete search history.

(56) References Cited

U.S. PATENT DOCUMENTS

| | | | |
|---|---|---|---|
| 4,766,062 A | 8/1988 | Diamond et al. | |
| 6,037,130 A | 3/2000 | Tyagi et al. | |
| 6,103,476 A | 8/2000 | Tyagi et al. | |
| 6,150,097 A | 11/2000 | Tyagi et al. | |
| 6,235,504 B1 | 5/2001 | Zhang et al. | |
| 6,451,535 B1 * | 9/2002 | Jenne et al. | 435/6 |
| 6,531,286 B2 | 3/2003 | Jayasena et al. | |
| 6,607,889 B1 | 8/2003 | Coull et al. | |
| 6,645,733 B1 | 11/2003 | Daksis et al. | |
| 6,699,661 B1 | 3/2004 | Kurane et al. | |
| 6,713,262 B2 * | 3/2004 | Gellibolian et al. | 435/6 |

OTHER PUBLICATIONS

Tyagi et al. Nature Biotechnology 14 : 303-308 (Mar. 1996).*
Yamamoto et al. Genes to Cells 5: 389-396 (2000).*
The Stratagene Catalog , p. 39 (1988).*
Li et al., "Folding versus self-assembling," *Chem. Eur. J.*, 9(19):4594-4601 (Oct. 12, 2003).
Wang et al., "Alternating DNA and π-Conjugated Sequences. Thermophilic Foldable Polymers," *J. Am. Chem. Soc*, 125(18):5248-5249 (Apr. 19, 2003).
Wang et al., "Foldable hybrid polymers and their sensory responses," Downloaded from <http://oasys2.confex.com/acs/225nm/techprogram/P604032.HTM>, (accessed Feb. 24, 2004) (Feb. 3, 2003).
Wang et al., "To Fold or to Assemble?," *J. Am. Chem. Soc.*, 125(5):1120-1121 (Jan. 10, 2003).

* cited by examiner

*Primary Examiner*—Ethan Whisenant
(74) *Attorney, Agent, or Firm*—Klarquist Sparkman, LLP

(57) ABSTRACT

Disclosed herein are novel probes, which can be used to detect and identify target molecules of interest in a sample. The disclosed probes can be used to monitor conformational changes induced by molecular recognition events in addition to providing signaling the presence and/or identity of a target molecule. Methods, including solid phase synthesis techniques, for making probe molecules that exhibit changes in their optical properties upon target molecule binding are described in the disclosure. Also disclosed herein are novel chromophore moieties, which have tailored fluorescent emission spectra.

57 Claims, 9 Drawing Sheets
(2 of 9 Drawing Sheet(s) Filed in Color)

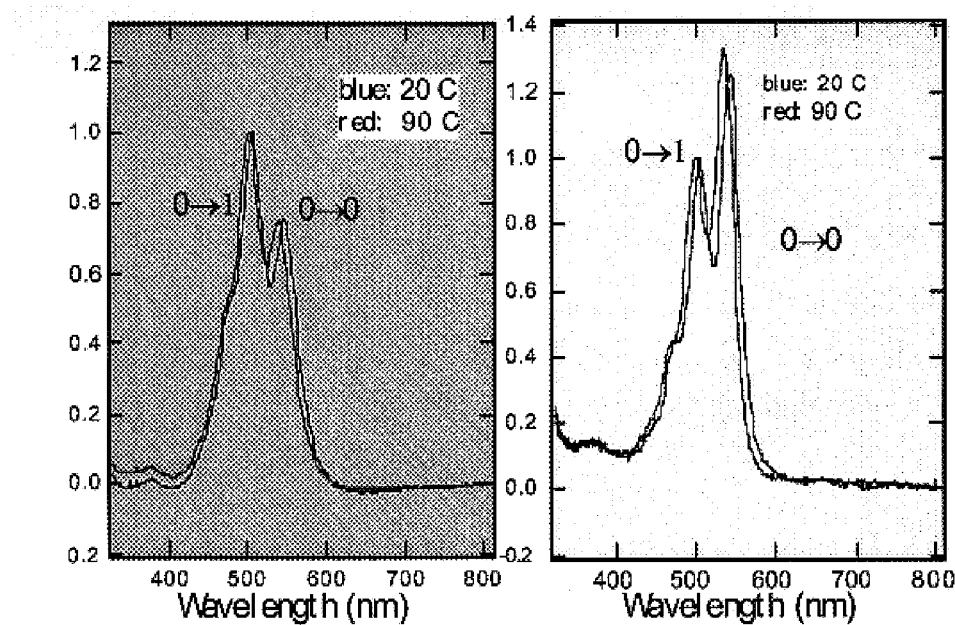
FIG. 5A  FIG. 5B
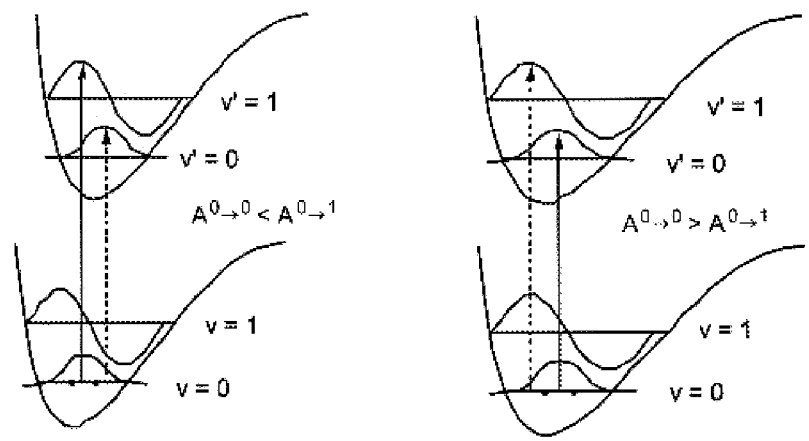
FIG. 5C  FIG. 5D

SEQUENCE LISTING

<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: Hairpin loop artificial sequence containing
      portion of AP1
      binding site.

<400> SEQUENCE: 1
atccggagtc agccggat                                                    18

<210> SEQ ID NO 2
<211> LENGTH: 18
<212> TYPE: DNA
<213> ORGANISM: Artificial Sequence
<220> FEATURE:
<223> OTHER INFORMATION: Complementary to hairpin loop artificial
      sequence containing
      portion of AP1 binding site.

<400> SEQUENCE: 2
atccggatga ctccggat                                                    18

<210> SEQ ID NO 3
<211> LENGTH: 22
<212> TYPE: DNA
<213> ORGANISM: Artificial Sequence
<220> FEATURE:
<223> OTHER INFORMATION: NF-kappa B binding site -continued artificial sequence

<400> SEQUENCE: 3
agttgagggg actttcccag gc         22

<210> SEQ ID NO 4
<211> LENGTH: 22
<212> TYPE: DNA
<213> ORGANISM: Artificial Sequence
<220> FEATURE:
<223> OTHER INFORMATION: NF-KB artifici
      al sequence variant

<400> SEQUENCE: 4
agttgagtgt tctttcccag gc         22

<210> SEQ ID NO 5
<211> LENGTH: 30
<212> TYPE: DNA
<213> ORGANISM: Artificial Sequence
<220> FEATURE:
<223> OTHER INFORMATION: Multiple cloning site (MSC) of bacteriop
      hage M13 artificial
      sequence.

<400> SEQUENCE: 5
catgcctgca ggtcgactct agaggatccc         30

<210> SEQ ID NO 6
<211> LENGTH: 30
<212> TYPE: DNA
<213> ORGANISM: Artificial Sequence
<220> FEATURE:
<223> OTHER INFORMATION: Multiple cloning site (MSC) of bacteri
      ophage M13, site 2.

<400> SEQUENCE: 6
tcatagctgt ttcctgtgtg aaattgttat         30

<210> SEQ ID NO 7
<211> LENGTH: 60
<212> TYPE: DNA
<213> ORGANISM: Artificial Sequence
<220> FEATURE:
<223> OTHER INFORMATION: Complementary sequence to
        MSC site 1 and 2.

<400> SEQUENCE: 7
gggatcctct agagtcgacc tgcaggcatg ataacaattt cacacaggaa acagctatga         60

<210> SEQ ID NO 8
<211> LENGTH: 18
<212> TYPE: DNA
<213> ORGANISM: Artificial Sequence
<220> FEATURE:
<223> OTHER INFORMATION: Random artificial target sequence.

<400> SEQUENCE: 8
atccggctga ctccggat         18

<210> SEQ ID NO 9
<211> LENGTH: 18
<212> TYPE: DNA
<213> ORGANISM: Artificial Sequence
<220> FEATURE:
<223> OTHER INFORMATION: Single mismatch complement to artificial
      random target sequence.

```
<400> SEQUENCE: 9
atccggctgt ctccggat                                               18

<210> SEQ ID NO 10
<211> LENGTH: 18
<212> TYPE: DNA
<213> ORGANISM: Artificial Sequence
<220> FEATURE:
<223> OTHER INFORMATION: Second single mismatch complement to
      artificial random target
      sequence.

<400> SEQUENCE: 10
atccggctga ctccgcat                                               18

<210> SEQ ID NO 11
<211> LENGTH: 18
<212> TYPE: DNA
<213> ORGANISM: Artificial Sequence
<220> FEATURE:
<223> OTHER INFORMATION: Double mismatch complement to target sequence.

<400> SEQUENCE: 11
atccggctca ctcccgat                                               18

<210> SEQ ID NO 12
<211> LENGTH: 18
<212> TYPE: DNA
<213> ORGANISM: Artificial Sequence
<220> FEATURE:
<223> OTHER INFORMATION: Second double mismatch complement to target
      sequence.

<400> SEQUENCE: 12
atccggctag ctccggat                                               18
```

FOLDABLE POLYMERS AS PROBES

CROSS REFERENCE TO RELATED APPLICATION

This application claims the benefit of U.S. provisional patent application No. 60/455,700, filed Mar. 18, 2003, which is incorporated herein by reference in its entirety.

STATEMENT OF GOVERNMENT RIGHTS

This invention was made with government support under contract number GM065306 awarded by the National Institutes of Health, contract number W-7405-ENG-36 awarded by the Department of Energy to the Los Alamos National Laboratories, and by subcontract number 28893001035 awarded by the Los Alamos National Laboratories. The government has certain rights in the invention.

FIELD OF THE DISCLOSURE

The present disclosure concerns reagents and methods for detecting specific target molecules.

BACKGROUND

Reagents and techniques that permit the specific detection of target molecules are important tools in many research areas and in clinical diagnostics. Many techniques have been developed for detecting target nucleic acid sequences, typically by detecting the hybridization of a complementary oligonucleotide probe sequence with a target sequence. These techniques often rely upon fluorescence resonance energy transfer (FRET), a phenomenon in which a change in fluorescence is caused by the interaction of two fluorophore groups.

One example of a class of oligonucleotide probes useful for detecting specific nucleic acid target sequences is referred to as "molecular beacons." Molecular beacons are nucleic acid sequences that contain both a fluorophore and group that quenches the fluorescence of the fluorophore (Tyagi and Kramer, *Nat. Biotech.* 14:303–308, 1996). By design, molecular beacons yield "on/off" signals, and usage of molecular beacons is mainly in detecting DNA through hybridization. Molecular beacons are limited because the 3' and 5' donors and acceptors need to be within nanometer-scale proximity for effective energy transfer to occur.

In general the detection of molecules using molecular recognition events other than complementary oligonucleotide hybridization is a more difficult proposition. Indeed, no single method is universally applicable. Specific proteins can be detected by using antibody-based assays, such as an enzyme-linked immunosorbent assay (ELISA). However, this technique can only be used to detect molecules for which antibodies exist. Furthermore, it is time-consuming and expensive to generate new antibodies, particularly antibodies that bind to a specific target portion of the analyte molecule. If the antibody is not directed against the functional portion of the analyte molecule, for example, when the analyte is a protein, the ELISA may not be able to distinguish an active from an inactive protein. Moreover, many molecules of interest, such as small molecules, tend to be refractory to antibody production.

SUMMARY OF THE DISCLOSURE

Disclosed herein are novel probes that are not limited solely to the detection of oligonucleotide hybridization. Moreover, the disclosed probes can be used to monitor changes in conformation induced by molecular recognition events in addition to providing simple on/off signals.

In one embodiment disclosed probes for detecting and identifying target molecules include plural interacting chromophore moieties and plural flexible linkers linking the chromophore moieties that are capable of selectively binding to a target biomolecule. Such probe molecules are sometimes called "foldamers" or "molecular accordions." The flexible linker typically has hydrophilic character and can be formed from any organic molecules, typically synthetic or naturally occurring oligomeric materials. For example, in certain embodiments the linker is assembled from natural, non-natural or a mixture of natural and non-natural amino acids. Similarly, in additional embodiments the flexible linker comprises a nucleic acid sequence, including DNA, RNA, or both, which can be assembled from natural, non-natural, or a mixture of natural, and non-natural nucleotides.

The disclosed probes can be designed to bind to any molecule of interest. For example, in one aspect, the disclosed probe molecules include oligonucleotides designed to selectively bind to a target, such as nucleotides and proteins, particularly nucleic acid binding proteins, such as transcription factors. Examples of such protein-binding nucleic acid sequences include, without limitation, AT-rich regions, AP-1 sites and NF-κB sites. Such sequences probes can be used to detect proteins, such as HMGA1, HMGB, NF-κB, c-Fos and c-Jun. In another aspect, the probes include oligonucleotides that bind to a second molecule, wherein a complex between the probe and the second molecule is recognized by a target molecule.

The chromophore moieties in the disclosed probes interact with one another, such that binding of or to a target molecule alters the interactions, resulting in a detectable change in the absorbance or emission of a chromophore. For example, certain chromophores include aromatic groups that tend to stack. Stacked chromophores typically exhibit different absorbance and emission properties than the corresponding de-stacked chromophores. Other chromophores engage in other non-covalent interactions that affect the absorption and emission properties of the chromophones. Certain probes are designed to include FRET pairs, which exhibit proximity-dependent fluorescence. Probes having a FRET pair include at least a first chromophore and a second chromophore having overlapping emission and absorption spectra. Additional embodiments include probes having a FRET cascade, for example, a FRET pair, plus a third chromophore moiety having an absorption overlapping with an emission of another chromophore moiety.

Also disclosed herein are novel chromophore moieties. Examples of such compounds include those according to the formulas:

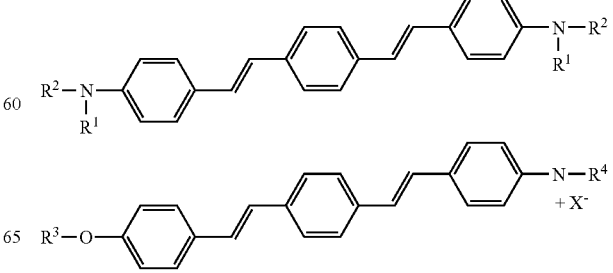

-continued

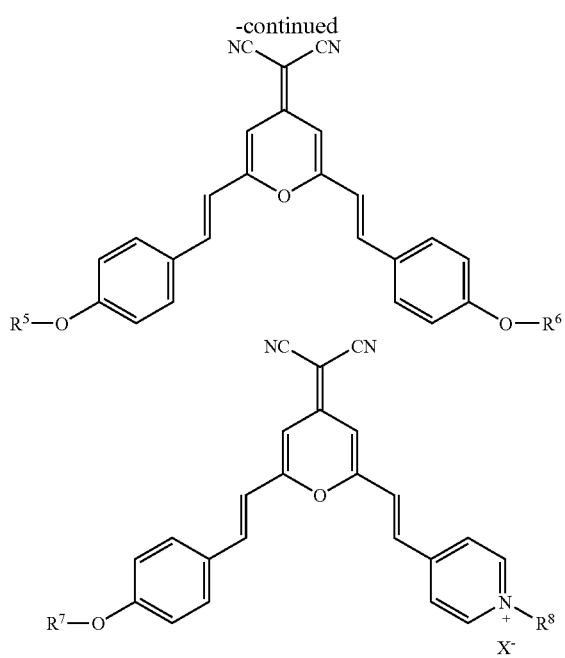

or salts thereof, wherein each $R^1$, $R^2$, $R^3$, $R^4$, $R^5$, $R^6$, $R^7$, $R^8$ can include a lower alkyl, aryl, carboxy, carboxy alkyl, phosphite, phosphoramidite, phosphate, or phosphoramidate group, and/or combinations thereof. In particular embodiments group such as $R^1$, $R^2$, $R^3$, $R^4$, $R^5$, $R^6$, $R^7$, $R^8$ include polyethylene glycol groups, which are optionally linked to another chromophore moiety, an oligonucleotide, or both.

Methods for making such chromophore-oligonucleotide conjugates also are disclosed, using, for example compounds such as:

wherein $R^9$ is a lower alkyl group, as building blocks.

The probes can include any number of chromophores and flexible linkers, but typically the disclosed probes include about the same number of chromophore moieties as flexible linker moieties. Usually the probes include from 2 to 10 chromophore moieties and from one to eleven linker groups, wherein the chromophore and linker groups alternate.

The probes can include additional functional groups in addition to the chromophore moieties and linking groups. For example, in some embodiments the chromophore groups are covalently linked to DNA by means of polyalkylene oxide groups, such as tetraethylene glycol moieties.

As a matter of convenience, the probes disclosed herein can be provided in a kit that typically includes a packaged combination of reagents in predetermined amounts with instructions for performing an assay.

Also disclosed herein are methods for using the disclosed probes, for example, to detect and/or quantify a biomolecule in vitro or in vivo. In one in vitro embodiment, the disclosed probes are arrayed on a substrate, to form a probe array.

One disclosed embodiment includes a protocol for identifying probes including foldamers that bind to a target analyte. In this embodiment, a library of probes, each including a plurality of chromophore moieties and plural variable linker portions, is created. Foldamers that bind to a target are selected and purified. The selected foldamers optionally can be amplified or subjected to one or more rounds of additional selection to produce additional or higher affinity foldamers. For example, oligonucleotide linker groups containing a variable region and a primer region can be incorporated into probes. Probes that bind to a desired target can be identified by their Amplification of nucleic acid foldamers by means of an error-prone amplification method can produce a population of nucleic acids, which can, for example be ligated with chromophore moieties to provide a new library of foldamers. Thus, the

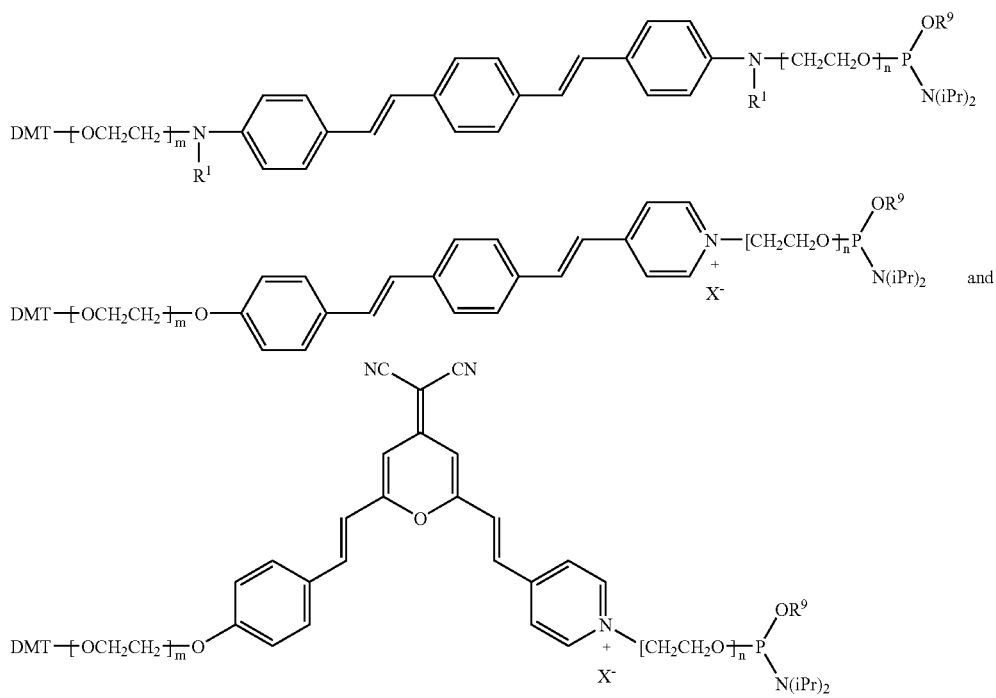

selection and amplification process can be repeated until a probe having a desired affinity for a particular target molecule is produced.

The foregoing and other features and advantages will become more apparent from the following detailed description of several embodiments, which proceeds with reference to the accompanying figures.

BRIEF DESCRIPTION OF THE FIGURES

The patent or application file contains at least one drawing executed in color. Copies of this patent with color drawings will be provided by the Patent and Trademark Office upon request and payment of the necessary fee.

FIG. 5A is a pair of overlaid optical absorption spectra for the probe depicted in FIG. 4 at both high and low temperature.

FIG. 5B includes optical absorption spectra at both 90° C. and 20° C. for the probe depicted in FIG. 4 following hybridization of the probe to a complementary DNA sequence.

FIG. 5C illustrates the absorption intensity ratio for the probe depicted in FIG. 4, $A^{0 \rightarrow 1} > A^{0 \rightarrow 0}$ at both high and low temperatures.

FIG. 5D illustrates the absorption intensity ratio for the probe depicted in FIG. 4, following hybridization of the probe to a complementary DNA sequence, $A^{0 \rightarrow 1} > A^{0 \rightarrow 0}$ at both 90° C. and 20° C.

SEQUENCE LISTING

Figure 1A:
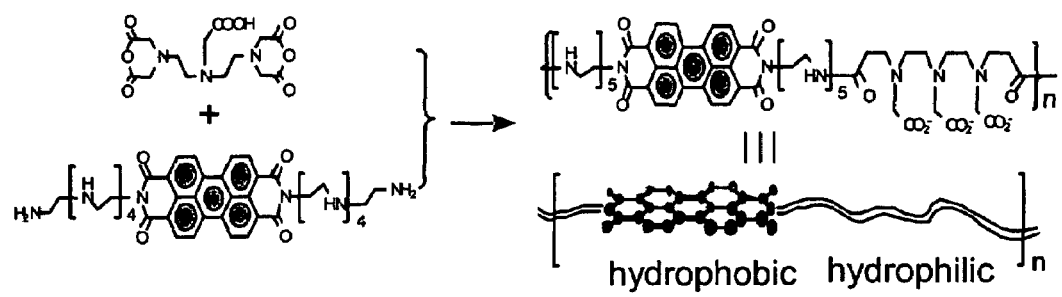
FIG. 1A illustrates the preparation of oligomers having alternating hydrophobic and hydrophilic segments.

The nucleic acid sequences listed in the accompanying sequence listing are shown using standard letter abbreviations for nucleotide bases, as defined in 37 C.F.R. 1.822. Only one strand of each nucleic acid sequence is shown, but the complementary strand is understood as included by any reference to the displayed strand. In the accompanying sequence listing:

SEQ ID NO: 1 is a model DNA sequence used to prepare thermophilic foldamers.

SEQ ID NO: 2 is a sequence complementary to SEQ ID NO: 1

SEQ ID NO: 3 is a NF-κB binding site.

SEQ ID NO: 4 is a variant of the NF-κB binding site of SEQ ID NO: 3.

SEQ ID NO: 5 is a sequence complementary to a portion of the multiple cloning site (MSC) of bacteriophage M13 (mp18) (SEQ ID NO: 7).

SEQ ID NO: 6 is a sequence complementary to a second portion of the multiple cloning site (MSC) of bacteriophage M13 (mp18) (SEQ ID NO: 7).

SEQ ID NO: 7 is the multiple cloning site (MSC) of bacteriophage M13 (mp18).

SEQ ID NO: 8 is a target DNA sequence.

SEQ ID NO: 9 is a single mismatch complementary sequence to SEQ ID NO: 8.

SEQ ID NO: 10 is a second single mismatch complementary sequence to SEQ ID NO: 8.

SEQ ID NO: 11 is a double mismatch complementary sequence to SEQ ID NO: 8.

SEQ ID NO: 12 is a second double mismatch complementary sequence to SEQ ID NO: 8.

DETAILED DESCRIPTION

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another respective embodiment. It will be further understood that the endpoints of each of the ranges are significant both in relation to the other endpoint, and independently of the other endpoint.

Terms

In this specification and in the claims which follow, reference will be made to a number of terms that can be understood to have the meanings discussed below.

"Optional" or "optionally" means that the subsequently described event or circumstance can but need not occur, and that the description includes instances where said event or circumstance occurs and instances where it does not.

"Chromophore" or "chromophore moiety" refers to a compound or derivative thereof that exhibits a detectable absorption of light. Certain chromophores also emit light, for example, fluorescent or phosphorescent chromophores.

Fluorescence resonance energy transfer (FRET) is the nonradiative transfer of electronic excitation energy from a donor to an acceptor molecule by a weak dipole-dipole coupling mechanism. When the emission of the donor chromophore overlaps the absorption of the acceptor chromophore, energy can flow from the excited donor to the acceptor, which typically emits a longer wavelength photon than that of the donor. The energy-transfer efficiency (E) decreases inversely proportional to $R^6$, the distance (R) between the donor and the acceptors, as $E=1/(1+(R/R_0)^6)$ (the Förster radius, $R_0$, is the distance corresponding to 50% energy transfer and depends on the photophysical properties of the dyes and their relative orientations). Thus, FRET is very sensitive to the distance (R) between fluorescent donors and fluorescent acceptors. Indeed, FRET allows distance measurements to be made on a nanometer scale, typically over a range of from about 2 to about 8 nanometers. Thus, FRET is well suited to the study of biological interactions of macromolecules.

In certain embodiments "FRET pairs" are employed, which are sets of fluorophores that can engage in fluorescence resonance energy transfer (FRET).

The probes disclosed herein include foldable oligomers and polymers ("foldamers") that recognize or bind to particular target molecules. The foldamers can be assembled from any suitable naturally occurring or synthetic monomer units, for example nucleotides, amino acids, or combinations thereof. For example, the foldamers used in exemplary disclosed probes are constructed from the major DNA and/or RNA nucleotides (see below). Working examples of probes described below use DNA oligomers as recognition elements.

The major DNA nucleotides include phosphorylated deoxyadenosine, deoxyguanosine, deoxycytidine, and deoxythymidine. RNA oligonucleotides, for example, as disclosed in U.S. Pat. No. 6,531,286 to Jayasena and Gold, also can be used to bind to and detect target molecules. The major nucleotides of RNA are adenosine, guanosine, cytidine, and uridine. The nucleotides disclosed herein also include nucleotides containing modified bases, modified carbohydrate moieties, and modified phosphate backbones, for example as described in U.S. Pat. No. 5,866,336 to Nazarenko et al., is incorporated herein by reference.

"Elevated temperature" refers to a temperature higher than room temperature.

Many molecules adopt secondary, tertiary and/or quaternary structures, and such molecules are said to "fold" when they adopt such structures. However, folding and unfolding are not absolute terms; rather such terms are relative and describe relative degrees of structures that are adopted by a given molecule.

Certain molecules and groups are described herein as "binding" to or "selectively binding" to, for example, a target molecule. These terms mean that the subject molecule or group is, for example, thought to be capable of binding to the target molecule under appropriate environmental conditions, such as concentration, solvent, and temperature. These and other environmental variables can be adjusted and selected by a person of ordinary skill in the art so that binding would occur.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Probe Molecules

Typical probe molecules disclosed herein alternate hydrophobic segments and hydrophilic segments in an oligomeric or polymeric sequence. Chromophore moieties are embedded in the hydrophobic sequences; quantum interactions between these chromophores, such as π-orbital overlap and resonance energy transfer, are very sensitive to the distance separating them, thus providing a yardstick in gauging folding and unfolding events. Moreover, such folding and unfolding events can be correlated to molecular recognition events. Fluorescence resonance energy transfer (FRET) between chromophores in foldamers is one example of such chromophore interactions. FRET is a particularly useful phenomenon because the high sensitivity with which such events can be monitored means that even single molecular events can be detected using fluorescence spectroscopy and microscopy. The hydrophilic segments used to connect the chromophore moieties allow the probe molecules to fold and enhance the solubility of the probes. The hydrophilic segments also include features that allow the probe to bind to a target molecule. The resultant molecular recognition properties of the probe result in molecular recognition-induced folding and unfolding events, which can induce changes in detectable chromophore properties, such as absorption or emission of photons at particular wavelengths.

Thus, examples of certain chromophores that can be used in the methods disclosed herein include fluorophores, such as those disclosed in U.S. Pat. No. 5,866,366 to Nazarenko et al. Suitable fluorophoric moieties include, without limitation, 4-acetamido-4'-isothiocyanatostilbene-2,2'-disulfonic acid, acridine and its derivatives such as acridine isothiocyanate, 5-(2'-aminoethyl)aminonaphthalene-1-sulfonic acid (EDANS), 4-amino-N-[3-vinylsulfonyl)phenyl] naphthalimide-3,5-disulfonate (Lucifer Yellow VS), N-(4-anilino-1-naphthyl)maleimide, anthranilamide, Brilliant Yellow, coumarin and its derivatives such as 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and its derivatives such as eosin isothiocyanate; erythrosin and its derivatives such as erythrosin B and erythrosin isothiocyanate; ethidium; fluorescein and its derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), and QFITC (XRITC); fluorescamine; IR144; IR1446; Malachite Green isothiocyanate; 4-methylumbelliferone; ortho-cresolphthalein; nitrotyrosine; pararosaniline; Phenol Red; B-phycoerythrin; o-phthaldialdehyde; pyrene and its derivatives such as pyrene butyrate and succinimidyl 1-pyrene butyrate; Reactive Red 4 (Cibacron .RTM. Brilliant Red 3B-A); rhodamine and its derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101, and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; and terbium chelate derivatives.

Other suitable fluorophores include thiol-reactive europium chelates that emit light at approximately 617 nm (Heyduk and Heyduk, *Analyt. Biochem.* 248:216–27, 1997; *J. Biol. Chem.* 274:3315–22, 1999).

Other suitable fluorophores include those selected from GFP, Lissamine™, diethylaminocoumarin, fluorescein chlorotriazinyl, naphthofluorescein, 4,7-dichlororhodamine, and the xanthene class of dyes (as described, for example, in U.S. Pat. No. 5,800,996 to Lee et al., incorporated herein by reference), and derivatives thereof. Other fluorophores known to those skilled in the art may also be used, for example those available from Molecular Probes (Eugene, Oreg.).

The fluorophores disclosed herein may be used as donor fluorophores, acceptor fluorophores or both. Particularly useful fluorophores have the ability to be attached to a linker and/or a recognition group, such as an oligonucleotide, peptide, or protein that binds to a target molecule. Ideally, selected fluorophores are stable against photobleaching, and have high quantum efficiency. In addition, the fluorophores for use in the same system are advantageously selected to have distinguishable emission spectra.

Examples of FRET pairs include those that use FAM as one member of the pair. FAM is most efficiently excited by light with a wavelength of 488 nm, emits light with a spectrum of 500 to 650 nm, and has an emission maximum of 525 nm. Thus, FAM is a suitable donor fluorophore for use with JOE, TAMRA, and ROX (all of which have their respective excitation maxima at 514 nm, and are not significantly stimulated by the wavelength of light that stimulates FAM).

The GFP mutant H9-40 (Tsien, 1998, *Ann. Rev. Biochem.* 67:509), which is excited at 399 nm and emits at 511 nm, may serve as a suitable donor fluorophore for use with BODIPY, fluorescein, rhodamine green and Oregon green. In addition, the fluorophores tetramethylrhodamine, Lissamine™, Texas Red, and naphthofluorescein can be used as acceptor fluorophores with this GFP mutant.

The fluorophore 3-($\epsilon$-carboxy-pentyl)-3'-ethyl-5,5'-dimethyloxacarbocyanine (CYA) is maximally excited at 488 nm and may therefore serve as a donor fluorophore for fluorescein or rhodamine derivatives (such as R6G, TAMRA, and ROX), which can be used as acceptor fluorophores (see Hung et al., *Analytical Biochemistry,* 243: 15–27, 1996). One of ordinary skill in the art can easily determine, using known techniques of spectrophotometry, the particular fluorophores that will make suitable donor-acceptor FRET pairs. One skilled in the art also will recognize that numerous combinations of fluorophores other than those specifically disclosed can be used.

Oligonucleotides are particularly useful for connecting chromophore moieties, because probes including nucleic acids that bind to a particular target can be amplified and "evolved," for example, using a SELEX™ protocol as disclosed in U.S. Pat. Nos. 5,707,796, 5,763,177, 5,580,737, and 5,567,588, each of which is incorporated herein by reference.

Examples of modified base moieties that can be incorporated into nucleotides at any position include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-sopentenyladenine, 1-methylguanine, 1-methylinosine, 2,2-dimethylguanine, 2-methyladenine, 2-methylguanine, 3-methylcytosine, 5-methylcytosine, N-6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, and 2,6-diaminopurine.

Examples of modified carbohydrate moieties that may be incorporated into a nucleotide include, but are not limited to: arabinose, 2-fluoroarabinose, xylose, and hexoses, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

With reference to FIG. 1, a first embodiment of the disclosed probes was prepared using molecules of the large $\pi$-conjugated chromophore, 3,4,9,10-perylene tetracarboxylic dianhydride as a building blocks and multiple repeating carboxylic groups ($CH_2COOH$) and ethylene amine units ($—CH_2CH_2NH—$) as flexible hinges. The resulting compounds have alternating planar hydrophobic regions and flexible hydrophilic disordered regions that can interact with water through electrostatic charges or H-bonds. Gel electrophoresis demonstrated that compounds synthesized in this manner have an average molecular weight equivalent to 7 kb of DNA. These materials demonstrate the preparation of probes having alternating hydrophobic and hydrophilic regions, wherein the hydrophobic regions include chromophores, and the hydrophilic regions of these polymers are flexible.

Figure 1B:
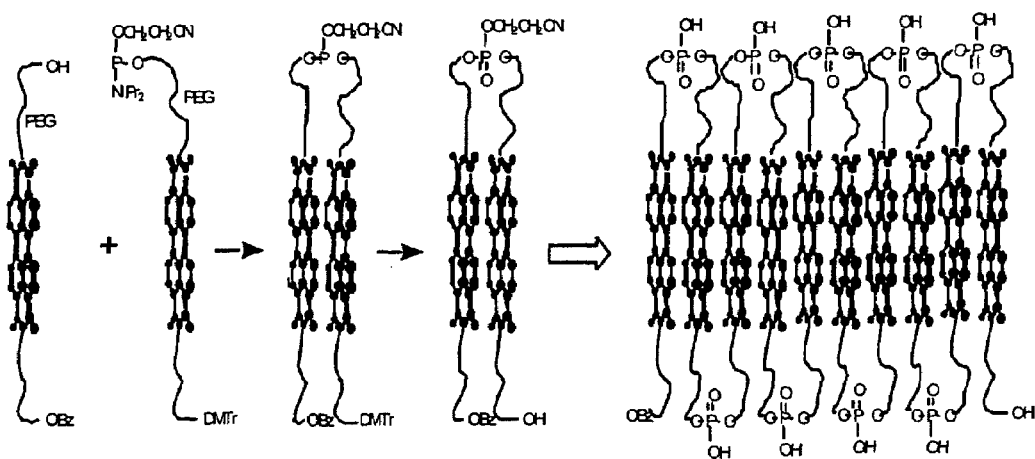
FIG. 1B illustrates the stepwise synthesis of a second type of oligomer having alternating hydrophobic and hydrophilic segments.

In another embodiment, foldable oligomers were constructed by stepwise addition of building blocks to a first building block (FIG. 1B). In the illustrated examples, the first building block is monobenzoylated bis-N,N-(2-(2-(2-(2-hydroxyethoxy)ethoxy)ethoxy)ethyl) perylene tetra-carboxylic diimide(HPTD). With continued reference to FIG. 1B, subsequently added building blocks are HPTD with one hydroxyl group protected with a DMT group (Kataoka and Hayakawa, *J. Org. Chem.* 64(16):6087–6089, 1999; Ling et al. *Carbohyd. Res.* 223:287–291, 1992). The building blocks are coupled via the incipient building block's phosphoramidite group to give the triester compounds illustrated in FIG. 1B (See, Noyori and coworkers, *J. Amer. Chem. Soc.*

123(34):8165–8176, 2001; Beaucage and Iyer, *Tetrahedron* 49(46):10441–10488, 1993; Oligonucleotide synthesis: A Practical Approach, Ed. Gait, M. J., IRL Press (Washington, D.C.), 1984; Sobol et al. *J. Biol. Chem.* 270(11): 5963–5978, 1995). The oligomer-growing end can then be activated via acid-mediated DMT removal to yield the corresponding free hydroxyl group necessary for chain extension. Using this method of coupling, followed by detritylation, specific oligomers including the dimer, trimer, tetramer, pentamer, and hexamer compounds were prepared and characterized. To date, oligomers up to undecamer size have been prepared using this effective synthetic strategy. Useful properties of such foldable oligomers are their monodisperse character and precisely controlled sequence, orientation, and folding.

Figure 2:
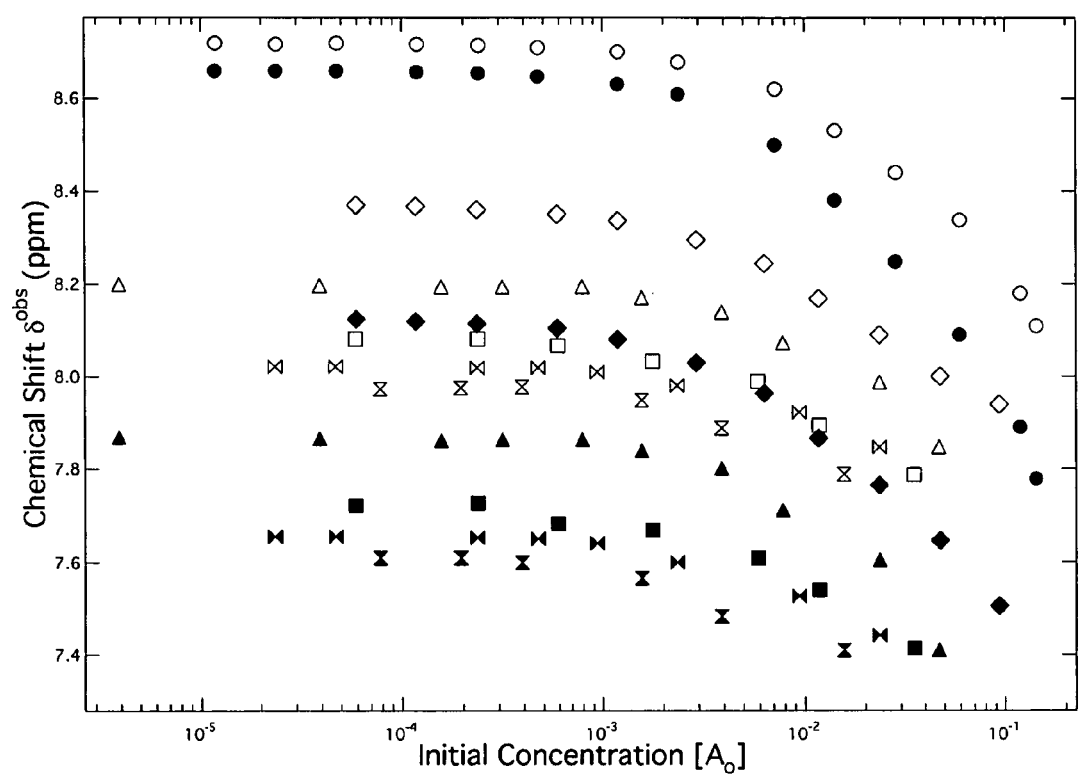
FIG. 2 is a graph recording the observed chemical shifts ($\delta$, ppm) for perylene aromatic protons versus initial concentration of oligomer ($A_0$, M); observed chemical shifts Ha (open) and Hb (filled) of monomer (circles), dimer (diamonds), trimer (triangles), tetramer (squares), pentamer (horizontal double triangles), and hexamer (vertical double triangles) as a function of the initial molar concentration of each species.

With reference to FIG. 2, the polyethylene glycol/perylene oligomers (dimer, trimer, tetramer, pentamer, and hexamer) described above exist as free folded structures in dilute solutions (<1 mM). Their free-folded structures are indicated by the up-field shift of their perylene aromatic proton resonances (Ha and Hb). The chemical-shift separation ($\Delta\delta$) between Ha (four outer protons) and Hb (four inner protons) is a reliable indicator of folded versus non-folded structures. The larger $\Delta\delta$ values observed for the folded structures arise because the inner proton (Hb) experiences a larger ring current than the outer proton (Ha) when the two aromatic rings are π-stacked. For the free monomer, $\Delta\delta$ is 0.061 ppm, whereas, in the folded dimer $\Delta\delta$ is 0.26 ppm (FIG. 2). Similarly, the folded trimer, tetramer, pentamer, and hexamer have $\Delta\delta$ values of 0.33, 0.38, 0.38, and 0.38 ppm, respectively, confirming that they all exist as folded structures, even in chloroform. Note that the Ha and Hb separation is very small for free monomer in dilute concentrations and is very large for the foldable oligomers 2–6 in dilute concentrations; this effect is caused by the ring current of the π-stacked perylene neighbors. As the oligomer concentration increases, the Ha and Hb resonance peaks shift further up-field, which is characteristic of folded oligomers that are self-assembling into larger nanostructures.

Figure 3A:
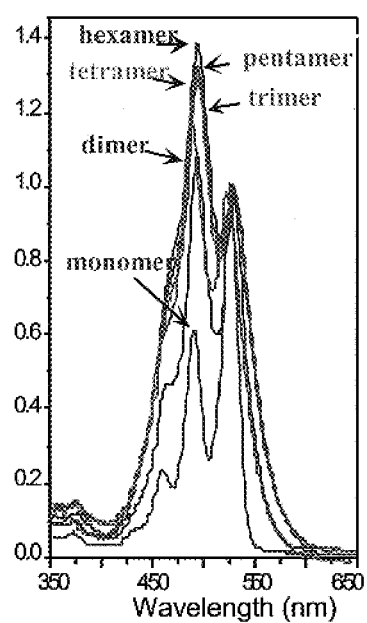
FIG. 3A includes overlaid absorption spectra (abs. vs. wavelength) of perylene-DNA monomer and oligomers at a 6.6 µM concentration of monomeric perylene units.
Figure 3B:
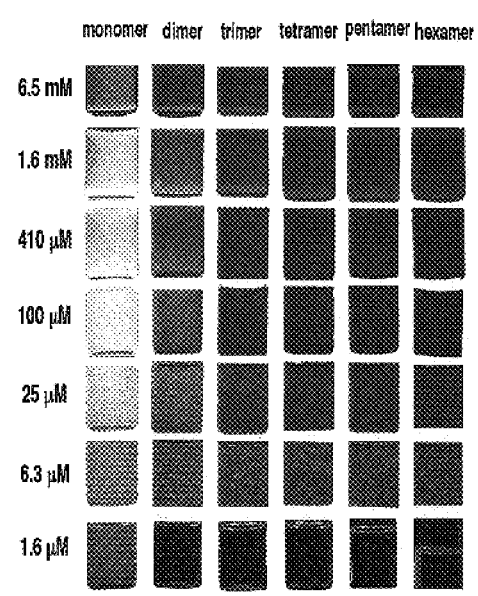
FIG. 3B is a photograph of fluorescence emission from various concentrations of perylene-DNA monomer and oligomer solutions, demonstrating that the folded oligomers have dramatically different emission spectra than the corresponding monomer at the same concentration.

The electronic absorption spectra of the linked perylene oligomers also have characteristic features that identify stacking of perylene units. In the "free" monomer, the intensity of 0→0 transition is about twice of that of 0→1 transition. In the folded structures, however, the intensity ratio is reversed, indicating that quantum interactions between π-electrons have greatly altered the optical properties. The intensity of vibronic bands are governed by the Franck-Condon overlap integral $<_{\chi_v}I_{\chi_{v'}}>$, and the folded structure favors absorption to higher excited vibronic states 0→v'=1 rather than 0→v'=0. Similarly, the photo-luminescence also favors emission to higher ground vibronic states (0→v, v=0, 1, 2, 3), thereby red-shifting the spectra. FIGS. 3A and 3B illustrate these phenomena, specifically, the photoluminescence of foldable oligomers at various concentrations excited at 365 nm. The dramatic feature is that the foldable oligomers have very distinct emission colors from the corresponding monomers. Monomers in this concentration region (1.6 µM–6.5 mM) emit green to yellow photons, whereas the foldable oligomers emit predominately red photons, with the exception that the dimer emits light having an orange red color.

Figure 4:
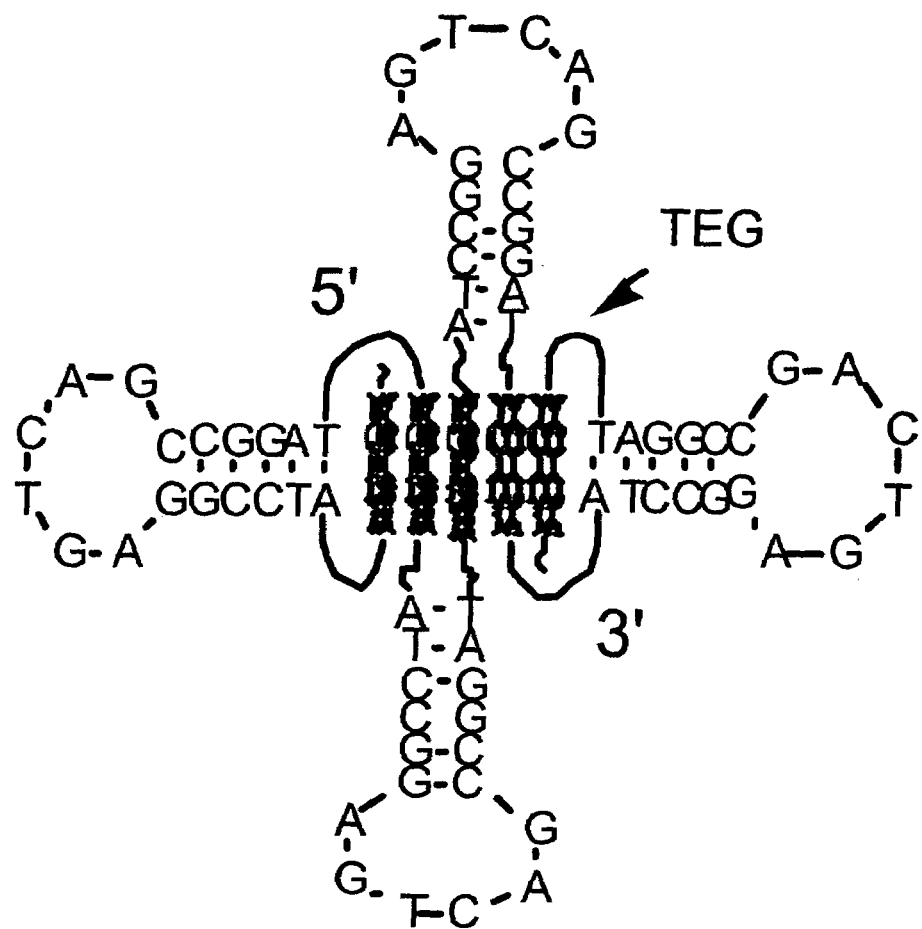
FIG. 4A is an optical absorption spectrum of a pentameric perylene-DNA (in this example the DNA sequence is a NF-κB regulatory sequence) probe.

Using solid-phase synthesis techniques, the probe compound depicted in FIG. 4 was synthesized. With reference to FIG. 4, the probe included a DNA oligonucleotide (5'-ATC-CGG-AGT-CAG-CCG-GAT-3') (SEQ ID NO: 1) linked to perylene chromophore moieties via flexible tetraethylene glycol loops to form a folded oligomer including five perylene chromophores and four single-strand foldable oligo-DNA chains (FIG. 4). The oligonucleotide was a hairpin loop containing part of the AP1 binding site (c-Fos/c-Jun). Indeed, the folded and unfolded probes had distinct absorption and emission features, as illustrated in FIGS. 5A–5D. The single-strand DNA included a six-base-pair stem in the loop between perylene chromophores to thermally stabilize the folded structure at 20–90° C. The linkage between the perylene unit and the DNA oligomer was tetraethylene glycol (TEG). In water, hydrophobic attractions drove the planar perylene unit to fold into ordered structures at room temperature and at elevated temperature, leaving the water-soluble single strand DNA on the periphery. Optical absorption spectra were used to demonstrate the probe folding, as illustrated in FIGS. 5A and 5B.

As illustrated in FIGS. 5A–5D, both the high-temperature (90° C., red curve in FIG. 5A) and low-temperature (20° C., blue curve in FIG. 5A) the absorption spectra have essentially the same features, with $A^{0\rightarrow 0}<A^{0\rightarrow 1}$ (FIG. 5C) being indicative of extensive folding of the polymer chain. Repeated temperature cycling between 20° C. and 90° C., does not eliminate the characteristic absorption features (FIGS. 4 and 5A), indicating stable thermophilic properties in folded probes. However, upon addition of equimolar amounts of the complementary strand (3'-TAG-GCC-TCA-GTA-GGC-CTA-5') (SEQ ID NO: 2) in an annealing buffer (10 mM Tris.HCl, 0.1 M NaCl, 1 mM EDTA) to the thermophilic hybrid polymer, the perylene π-stacking was disrupted, as indicated by the reversal of $A^{0\rightarrow 0}/A^{0\rightarrow 1}$ from 0.76 to 1.4 (FIGS. 5B, 5D). This result demonstrates that the disclosed foldable oligomer probes can be used as robust biosensors to detect specific oligonucleotides. Specifically, although this foldable oligomer with bound complementary DNA melts, losing its double helical structure, at 58° C., it still cannot fold above its melting temperature, as manifested by the intensity ratio of 0→0 and 0→1 transitions, and the presence of a complementary target DNA strand prohibits the folding processes even when the duplex DNA has melted (FIGS. 5B, 5D), indicating that target DNA can be detected at high temperature as well.

Figure 6:
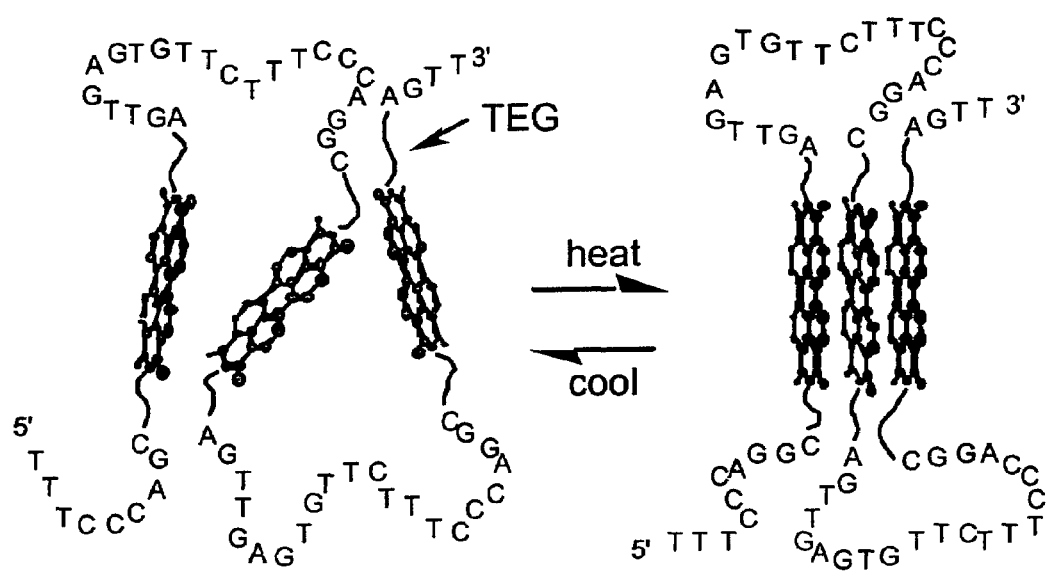
FIG. 6 illustrates the thermophilic folding character of a representative perylene-DNA probe.

The above-described optical properties are general phenomena that have been replicated for other foldable oligomers containing perylene chromophore units but different DNA oligonucleotides, including the NF-κB binding site (5'-A-GTT-GAG-GGG-ACT-TTC-CCA-GGC-3') (SEQ ID NO: 3) and a variant of the NF-κB regulatory sequence (5'-A-GTT-GAG-TGT-TCT-TTC-CCA-GGC-3'; three variations are in bold letters) (SEQ ID NO: 4) (FIG. 6).

Figure 7A:
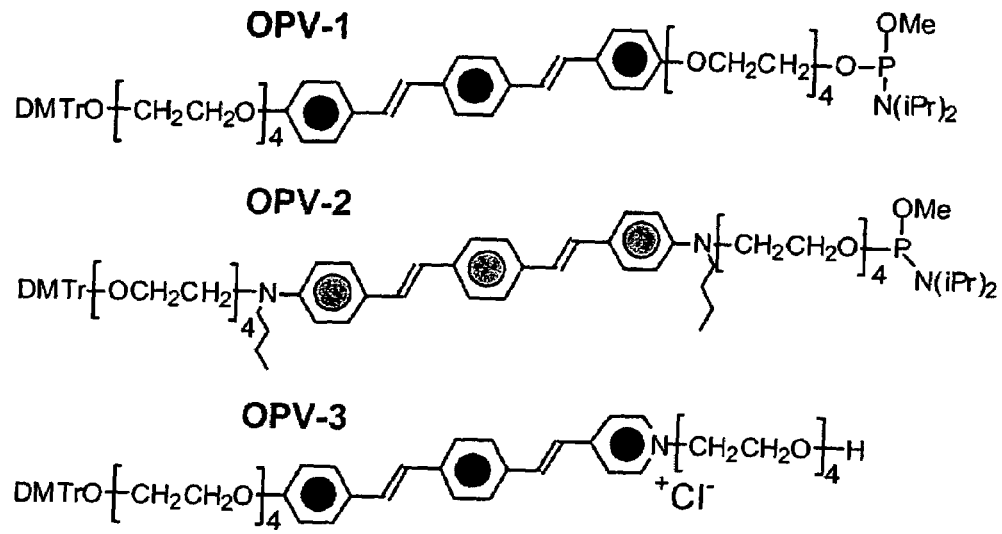
FIG. 7A illustrates the structures of exemplary (OPV-1, OPV-2, and OPV-3) oligo-phenylene vinylene-derived (OPV) chromophore moieties that have been tuned with substitutions at the chromophore ends to generate different fluorescence emissions, so that (upon excitation at 365 nm) OPV-1 emits blue light, OPV-2 emits green light, and OPV-3 emits light in the red-orange region.
Figure 7B:
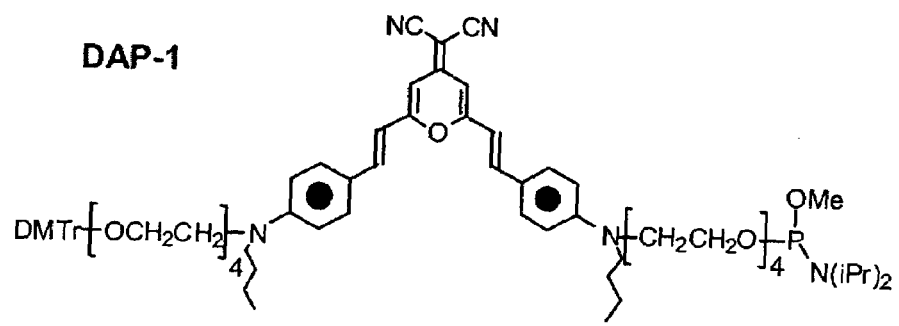
FIG. 7B illustrates the structure of DAP-1, which has been tuned for light emission in the red region upon being excited at 365 nm.

Also disclosed herein are two novel series of fluorescent chromophores. The first is based upon oligo-phenylene vinylene (OPV), and the second is based on dicyanomethylene aminostyryl 4H-pyran, or DAP (FIGS. 7A and 7B). The disclosed chromophores were modified or "tuned" to emit light of a particular wavelength. For example, a blue-light emitter was obtained by double oxygen substitution at the para position of the phenyl groups in OPV-1 (FIG. 7A), and green-light emission was obtained by replacing the para oxygen atoms with amino groups to yield OPV-2 (FIG. 7A). OPV-3 was designed to possess intramolecular charge-transfer character, which lowers the band gap, yielding a red shift in the fluorescent emissions. Thus, the phenoxy/pyridinium salt combination of OPV-3 depicted in FIG. 7A yields an orange-light emission.

DAP-1 (FIG. 7B) exhibits excellent red fluorescence. Additional chromophores based upon the DAP core are envisioned. For example, the para amino group of DAP-1 can be replaced with an alkoxy group to fine-tune the chromophore's emission spectrum for optimized visualization.

Figure 8A:
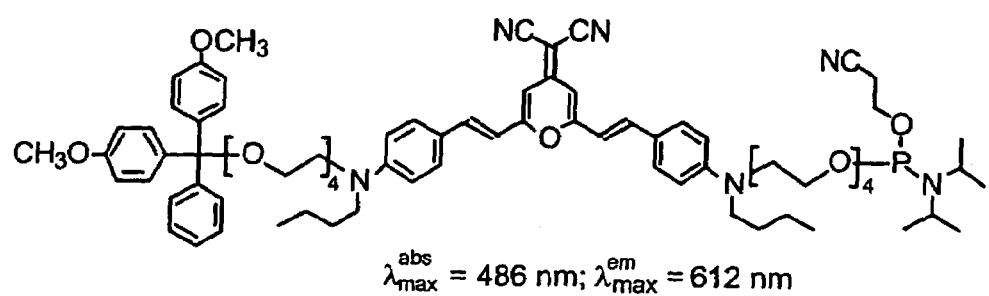
FIG. 8A depicts the structure of a protected DAP-1 monomer suitable for automated oligonucleotide synthesis.
Figure 8B:
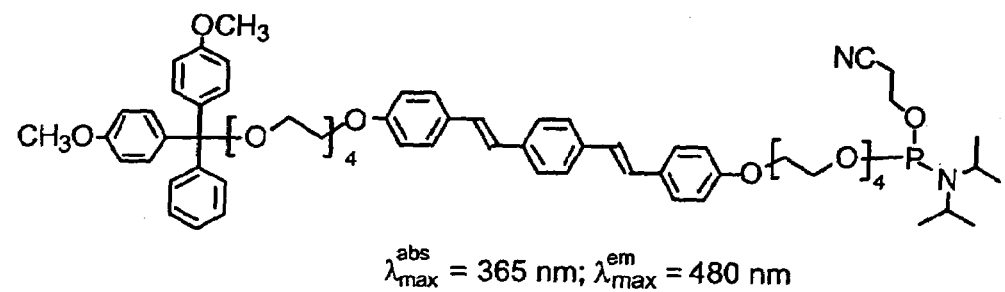
FIG. 8B depicts the structure of a protected OPV-1 monomer suitable for automated oligonucleotide synthesis.

Foldamers with alternating hydrophobic and hydrophilic structures were prepared incorporating the chromophores described above. FIG. 8A depicts an embodiment of a useful building block for incorporating the DAP-1 chromophore into probe molecules using solid-phase synthesis. Likewise, FIG. 8B depicts an embodiment of a useful monomer for incorporating OPV-1 chromophore moieties into probe molecules using solid-phase synthesis. The chromophore moieties illustrated in FIGS. 8A and 8B are suitable for use in the same probe, because DAP-1 emits in the red region with $\lambda_{max}$~612 nm and OPV-1 emits in the blue region, with an emission maximum at 480 nm. In addition to being orthogonal with respect to fluorescent emissions, the absorption maximum of the DAP-1 red chromophore (486 nm) overlaps with the fluorescent emission of the OPV-1 blue chromophore. Thus, DAP-1 and OPV-1 are well-suited for use in the same systems.

With continued reference to FIGS. 8A and 8B, DAP-1 includes flexible tetraethylene glycol (TEG) linkers attached to both amino groups of the chromophore moiety, yielding two hydroxyl groups at either end of the chromophore. These tetraethylene glycol moieties can be readily replaced with different groups, without significantly affecting the core chromophore moiety. For example, other linker groups, such as substituted or unsubstituted alkyl groups, or oligoethylene glycol groups can be attached to the amino groups. One hydroxyl group was protected with a removable blocker, dimethoxytrityl (DMT) group and the other was activated with a phosphoramidite group. The OPV-1 blue emitter is similarly functionalized with a removable DMTr protection and an efficient phosphoramidite coupler for hydroxyl groups (FIG. 8B). A similar protection/activation strategy is typically used for oligonucleotide building blocks in automated solid-phase oligonucleotide synthesis (See, Noyori and coworkers, J. Amer. Chem. Soc. 123(34):8165–8176, 2001; Beaucage and Iyer, Tetrahedron 49(46):10441–10488, 1993; Oligonucleotide synthesis: A Practical Approach, Ed. Gait, M. J., IRL Press (Washington, D.C.), 1984; Sobol et al. J. Biol. Chem. 270(11): 5963–5978, 1995). Indeed, the chromophore moieties are conveniently incorporated into DNA in nearly quantitative yield.

Using solid-phase synthesis, OPV-1 and DAP-1 were introduced into the foldable polymer with the same oligonucleotide repeating units as shown in FIGS. 4 and 6. In these examples, three chromophores moieties are incorporated. The sequence of the three chromophores is OPV-1, DAP-1, and OPV-1, which yields a folded structure with a chromophore line-up of blue-red-blue.

When this foldable polymer is dotted (1 µL) on a microscope slide, the dried spot emits orange-red color fluorescence. However, when this foldable polymer is incubated with a complementary strand and then dotted (1 µL) on a microscope slide under the same conditions, the dried spot emits yellow green fluorescence. These results demonstrate that, without complementary-strand DNA, the probe can fold and thus bring hydrophobic fluorescent chromophores into close proximity. Proximity of the chromophore moieties results in fluorescence-energy transfer, which produces dominant emissions in the red region of the spectrum. With complementary target DNA, the rigid DNA duplex prevents fluorescent chromophores from coming in close proximity to each other, resulting in domination of blue emission and a green observed (net) color. Because the foldable polymer probes include very sensitive fluorescent chromophore moieties, the disclosed probes can provide detection sensitivity at the single macromolecule level. Indeed, single-nucleotide polymorphisms (SNPs) in the complementary target sequences can be detected using the disclosed probe foldamers.

Specifically, using a DNA-blue chromophore moiety-DNA-red chromophore moiety-DNA-blue chromophore moiety-DNA probe, wherein the red chromophore moiety is DAP-1 and the blue chromophore moiety is OPV-1 and DNA has a sequence of 5'-ATC-CGG-AGT-CAG-CCG-GAT-3' (SEQ ID NO: 8) except the terminal DNA sequences which has been truncated.

This foldamer has been tested with its complementary pair, along with various mismatched sequences to evaluate its selectivity and the feasibility of using foldamers as DNA probes. As discussed above, with the control sample, the overlapping blue-red-blue chromophores yield strong FRET, and the control exhibits orange-red emission. In the presence of complementary target DNA, the sample in the solid state emits yellow-green color because the foldamer probe cannot fold due to the formation of the DNA duplex. In contrast, incubation of SEQ ID NO: 9, which has a single mismatched base in the middle of the sequence, with the probe, followed by drying, results in a dominant bright-yellow emission by the probe. When the mismatch is introduced toward the end 3' end of the DNA oligonucleotide (as in SEQ ID NO: 10), the difference between target and one mismatch becomes even more marked. The OM2 spot emits a significant number of red photons, making the difference spectrum vividly green. In summary, identification and differentiation of target oligonucleotides from oligonucleotides differing by one nucleobase is enabled using the disclosed probe molecules.

Similarly, sequences having two mismatch bases can be distinguished from a target sequence by the disclosed probe molecules. Specifically, incubation of SEQ ID NO: 8 with mismatch sequences (SEQ ID NO: 11 and SEQ ID NO: 12) results in considerable red fluorescent emissions in both cases, resulting in the difference spectrum between target and the mismatch sequences being green. These results indicate that sequences with greater with one or more one base mismatch can be readily distinguished from a sequence that is complementary to a given target oligonucleotide.

Molecular Recognition Targets

The probes disclosed herein can be utilized as in vitro and in vivo tools to analyze various biological processes. The disclosed probes are particularly useful in the context of nucleic acid-nucleic acid and protein-nucleic acid interactions. For example, probes that include a DNA oligomer linking one or more chromophore moieties can be used to detect complementary nucleic acids or proteins that bind to the DNA oligomer.

In principle, any binding event that induces a change in the conformation of the hydrophilic segments used to link the chromophore moieties can be detected. For example, where the probes include a DNA oligomer, binding events that induce conformational changes, such as a bend in the DNA structure, can be detected. Similarly, a folded or "bent" hydrophilic segment can be induced to unfold by a binding event. One example of this phenomenon is the unfolding of hairpin DNA upon binding to the DNA of a complementary oligonucleotide.

Figure 9:
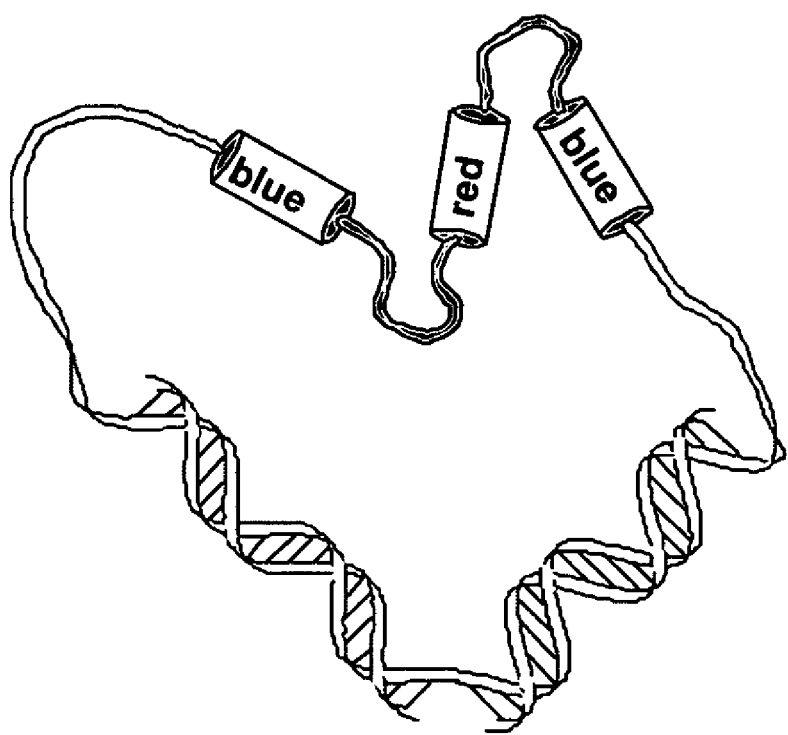
FIG. 9 depicts two nucleotide strands coupled to opposite ends of oligomeric interacting chromophores hybridized to a template complementary nucleotide strand.

The probes disclosed herein are extremely sensitive. For example, the repair of a nick in a DNA sequence can be monitored using disclosed examples of the probe molecules. See, for example FIG. 9 and example 21, below.

Certain working embodiments employed HMGA1 proteins and their interactions with AT-rich DNA sequences to demonstrate the detection of protein-nucleic acid interactions. The high-mobility-group (HMG) proteins HMGA1 (formerly HMG I/Y), a family of non-histone, chromosomal proteins consisting of HMGA1a (107 amino acid, ~11.7 kDa), HMGA1b (96 amino acid, ~10.6 kDa), and HMGA2 (109 amino acid, ~12 kDa), are known as architectural transcription factors because they bind to DNA and interact with various transcriptional factors. The level of expression of HMGA1 genes is maximal during embryonic development and in rapidly proliferating cells, whereas their expression in non-dividing adult cells or tissues is low (Bustin and Reeves, *Prog. Nucleic Acid Res. Mol. Biol.* 54:35–100, 1996, incorporated herein by reference). The exceptionally high level of HMGA1 gene products in the transformed cells has been correlated to the increasing degrees of malignancy or metastatic potentials (Tallini and Dal Cin, *Adv. Anat. Pathol.* 6:237–46, 1999; Reeves R. *Environ. Health Perspect.* 108:803–9, 2000).

The correlation is so consistent and wide-spread that it has been suggested that the high level of expression of HMGA proteins are diagnostic markers of both neoplastic transformation of cells (Giancotti et al. *Cell Res.* 184:538–45, 1989; Manfioletti et al. *Nucleic Acids Res.* 19:6793–7, 1991) and metastatic tumor progression (Bussemakers et al. *Cancer Res.* 51:606–11, 1991; Tamimi et al. *Cancer Res.* 53:5512–6, 1993). To date, the published literature demonstrates a nearly perfect correlation between HMGA over-expression, neoplastic transformation, and tumor progression in every type of cancer. Therefore, convenient bio-probes that can identify and quantify the level of HMGA1 are useful in the study of abnormal transformation or tumor progression in cells.

In one example, the presence of the DNA binding protein HMGA1 was determined using a three-chromophore probe having a thirty base DNA oligonucleotide on each end; sequences of these two strings are complementary to two contiguous regions at the multiple cloning site (MSC) of bacteriophage M13 (mp18). The sequence on the 5'-end of the probe was 5'-CATGCC-TGCAGG-TCGACT-CTA-GAG-GATCCC-accordion, (SEQ ID NO: 5) whereas the sequence on the 3'-end of the accordion was accordion-TCATAG-CTGTTT-CCTGTG-TGAAAT-TGTTAT-3' (SEQ ID NO: 6). The sequence of the 60 bases was 5'-GGGATC-CTCTAG-AGTCGA-CCTGCA-GGCATG-ATAACA-ATTTCA-CACAGG-AAACAG-CTATGA-3'.

Thus, the probe, when hybridized to its complementary 60-base single stranded DNA, has a nick that provides hinge-like flexibility. Although the accordion has red fluorescence in the solid, it emits pure blue color in solution when the blue chromophore is excited. However, upon addition of HMGA1 protein to the blue-emitting solution, a distinct fluorescent color change from blue to pink is observed, which demonstrates HMGA1 binding. This accordion is specific to HMGA1 and does not respond to HMGB, a closely related family member, under the same conditions. A corollary to this observation is that HMGA1 binds and bends the double strand DNA, thus effectively relaxing the strain on the probe. As a result, the individual optically active chromophores of the accordion come closer and FRET occurs, which switches the fluorescence from blue to pink. This example demonstrates that proteins can be identified and even closely related proteins can be distinguished using the presently disclosed probe molecules.

EXAMPLES

The foregoing disclosure is further explained by the following non-limiting examples.

General Methods

Solvents and reagents were purified where necessary using literature methods*. In particular, N,N-dimethylformamide (DMF) was distilled from 4 Å MS (molecular sieves) under reduced pressure and stored under argon. Acetonitrile (MeCN) was heated under reflux over calcium hydride and distilled under argon. Where not otherwise specified, reagents were purified in accordance with: Purification of Laboratory Chemicals, $3^{rd}$ Edition, Perrin and Armarego, Eds. Pergamon Press.

MALDI Mass Spectra were obtained with an ABVS-2025 spectrometer. Elemental analyses were performed by the University of Illinois, Microanalysis Lab, School of Chemical Sciences, 151 Roger Adams Lab, Urbana, Ill. 61801 USA. $^1$H NMR spectra were recorded with a Bruker Mercury 300 (300-MHz) spectrometer for solutions in $CDCl_3$ ($CD_3OD$), $CDCl_2CDCl_2$, or DMSO-$d_6$ at ambient temperature. $^{13}$C-NMR spectra were recorded at 75.48 MHz with a Bruker Mercury 300 spectrometer for solutions in DMSO-$d_6$ adopting 39.50 ppm for the central line of DMSO-$d_6$ at ambient temperature or solution in $CDCl_3$ ($CD_3OD$) adopting 77.23 ppm for the central line of $CDCl_3$. $^{31}$P-NMR chemical shifts were reported in ppm using 85% $H_3PO_4$ as an external reference. Reactions were monitored by thin-layer chromatography (TLC) on a precoated plate of silica gel 60 $F_{254}$ (EM Science). Column chromatography was performed on silica gel 60 (230–400 mesh, EM Science).

The folding equilibrium constant ($K_{fold}$) was determined using UV-Vis spectroscopy as follows: The equilibrium constant in 1,1,2,2-tetrachloroethane (TCE) was determined by modeling the intensity ratio of the 0→0 transition and 0→1 transition. The unfolded dimer spectrum was modeled with the free monomer at dilute concentration in $CHCl_3$. The folded dimer was modeled with dimer in $CHCl_3$, which exist exclusively as the folded structure. The two spectra were then divided by the corresponding concentrations to yield spectra of $\epsilon_{fold}(\lambda)$ and $\epsilon_{unfold}(\lambda)$. The observed UV-vis spectra were then fitted to eq. (2) at various temperatures.

$$A^{obs}(\lambda) = C_{fold}\epsilon_{fold}(\lambda) + C_{unfold}\epsilon_{unfold}(\lambda) \qquad (2)$$

The cell thickness is 1 cm and $C_{fold}$ and $C_{unfold}$ are concentrations of the folded and unfolded species, respectively. The equilibrium constant $K_{fold}$ is determined by eq. (3).

$$K_{fold} = C_{fold}/C_{unfold} \qquad (3)$$

Example 1

This example describes the preparation of p-toluenesulfonic acid 2-[2-[2-(2-hydroxyethoxy)ethoxy]ethoxy] ethyl ester. To a solution of p-toluenesulfonyl chloride (22 g, 0.12 mol) in 200-mL dry $CH_2Cl_2$ (4 Å activated molecular sieves, 3 days) at 0° C., was added tetraethylene glycol (18 mL, 0.10 mol) and dry triethylamine (NaOH, pellets 3 days) (22 mL, 0.16 mol). The reaction mixture was then stirred for 2 h at 0° C., and left overnight at room temperature (RT) under argon. Detection of the products on TLC plates was accomplished using UV light or phosphomolybdic acid solution (10% PMA in EtOH). After elimination of the precipitate by filtration, the solution was evaporated under reduced pressure. The residue was purified by chromatography on a silica-gel column eluted with EtOAc/Hexane (80:20 to 100:0), and the desired product was obtained (12 g, 33% yield) as a colorless oil: $R_f$ 0.2 (EtOAc).

Example 2

This example describes the preparation of 2-[2-[2-(2-azidoethoxy)ethoxy]ethoxy]ethanol. A solution of monotosyl tetraethylene glycol (6 g, 17.2 mmol) and sodium azide (1.7 g, 26.2 mmol) in 50 mL of acetonitrile was heated under reflux (at 100° C. oil bath) for 36 hrs. After return to RT, 50 mL of water was added and the mixture was extracted with $CH_2Cl_2$. Detection of the products on TLC plates was accomplished using sulfuric acid solution (25.0 mL of conc. sulfuric acid, 12.6 g of ammonium molybdate, 0.57 g of cerium sulfate, and 225.0 mL of deionized water). The organic phase was then dried on $MgSO_4$ and concentrated under reduced pressure. The residue was chromatographed on a silica-gel column eluted with EtOAc. The product was obtained as a colorless oil (3.3 g, 89% yield): $R_f$ 0.5 (EtOAc); $^1$H-NMR (CDCl$_3$) δ3.77–3.59 (m, 14H, $CH_2OCH_2$, $HOCH_2$), 3.40 (t, J=5.0 Hz, 2H, $CH_2N_3$).

Example 3

This example describes the transformation of the azide product from example 2 to 2-[2-[2-(2-aminoethoxy)ethoxy]ethoxy]ethanol. The azido product from example 2 (3.3 g, 15.1 mmol), triphenylphosphine (4.4 g, 16.8 mmol), and water (405 mg, 22.5 mmol) were mixed with 20-mL THF. After the solution was stirred for 4 hrs. at RT, the solvent was eliminated under reduced pressure and the residual product was purified on a silica-gel column that was eluted with $CHCl_3/CH_3OH/Et_3N$ (3:3:1). The desired compound was obtained as colorless oil (2.5 g, 86% yield): $R_f$ 0.4 (CHCl$_3$/CH$_3$OH/Et$_3$N, 3:3:1). Detection of the products on TLC plates was accomplished using a sulfuric acid solution (25.0 mL of conc. sulfuric acid, 12.6 g of ammonium molybdate, 0.57 g of cerium sulfate, and 225.0 mL of deionized water) and/or ninhydrin test solution (a mixture of solution i, ii, and iii: (i) 1 mL of 0.1 M aqueous potassium cyanide diluted to 50 mL with pyridine; (ii) 2.5 g of ninhydrin in 50 mL of ethanol; (iii) 40 g of phenol in 10 mL of ethanol). $^1$H-NMR (CDCl$_3$) δ3.76–3.51 (m, 14H, $CH_2OCH_2$, $HOCH_2$), 2.82 (t, J=4.9 Hz, 2H, $CH_2N$).

Example 4

This example describes two methods for the preparation of bis-N,N'-(2-(2-(2-(2-hydroxyethoxy)ethoxy)ethoxy)ethyl)perylenetetracarboxylic diimide.

Method A: 2-[2-[2-(2-Aminoethoxy)ethoxy]ethoxy]ethanol (2.6 g, 13.5 mmol), perylenetetracarboxylic dianhydride (2.2 g, 5.6 mmol), and triethylamine (25 mL, 180 mmol) were mixed with 50 mL of dry DMSO (4A activated MS, 3 days) in a 250-mL flask under argon. After the reaction mixture was stirred for 4 h at 150° C., the reaction solution was cooled to 80° C. and transferred to a 1000-mL flask. A mixture of 600 mL 10% aqueous HCl and 300 mL methanol was added to the reaction solution, then the solution was stirred for additional 2 hours at 60° C. After the mixture was cooled to RT overnight, the precipitate was collected using paper filter. The resulting collection was washed with 400 mL water, and the water layer was re-extracted with 50 mL chloroform. The filtrate could be extracted with chloroform to gain more products, but these products were contaminated and needed column purification. The combined organic layer was concentrated to give the crude title product; further purification was carried out on a silica-gel column eluted with $CH_2Cl_2/CH_3OH$ (5:1). Detection of the products on TLC plates was accomplished using UV light or sulfuiric acid solution (5% conc. sulfuric acid in EtOH). The title compound was obtained as dark-red solid (3.6 g, 86% yield): $R_f$ 0.4 ($CH_2Cl_2/CH_3OH$, 10:1). $^1$H-NMR (60–70 mg/0.5 ml; CDCl$_3$/CD$_3$OD/100/5) δ7.96 (d, 4H, J=8.1 Hz, aromatic ring), 7.61 (d, 4H, J=8.1 Hz, aromatic ring), 4.32 (t, 4H, J=5.7 Hz, $CH_2N$), 3.65–3.29 (m, 28H, CH2OCH2, $HOCH_2$); $^{13}$C-NMR (60–70 mg/0.5 ml; CDCl$_3$/CD$_3$OD/100/5) δ162.7, 133.1, 130.4, 128.1, 124.7, 122.5, 122.4, 72.9, 70.79, 70.76, 70.4, 70.2, 68.0, 61.6, 39.5. $^1$H-NMR (DMSO-d$_6$) δ7.13 (bd, 4H, aromatic ring), 6.92 (bd, 4H, aromatic ring), 4.59 (t, 4H, J=5.7 Hz, $CH_2N$), 3.65–3.29 (m, 28H, CH2OCH2, $HOCH_2$); $^{13}$C-NMR (DMSO-d$_6$) δ161.2, 131.4, 128.8, 125.9, 122.6, 120.2, 72.3, 69.8, 69.7, 69.6, 66.5, 60.2, 45.67. MS (MALDI): m/z 765.82 [M+Na]$^+$. Anal. Calcd. for $C_{40}H_{42}N_2O_{12}$ (742.77): C, 64.68; H, 5.70; N, 3.77. Found: C, 64.24; H, 5.52; N, 3.83.

Method B: the azido product-2-[2-[2-(2-azidoethoxy)ethoxy]ethoxy]ethanol (0.5 g, 2.6 mmol) and perylenetetracarboxylic dianhydride (0.4 g, 1.0 mmol) were mixed with 5 mL of dry DMF (4A activated MS, 3 days) in a 25-mL flask under argon. The mixture was heated to 150° C. (oil bath 155° C.) for 20 hrs. with stirring under argon and cooled to room temperature. The solvent was removed in vacuum and the residue was subject to a silica gel column that was eluted with $CH_2Cl_2/CH_3OH$ (8:1 to 5:1) to give the title product (490 mg, 62% yield).

Example 5

This example describes the monobenzoylation of bis-N,N'-(2-(2-(2-(2hydroxyethoxy)ethoxy)ethoxy)ethyl) perylenetetracarboxylic diimide. To a solution of bis-N,N'-(2-(2-(2-(2-hydroxyethoxy)ethoxy)ethoxy)ethyl) perylene tetracarboxylic diimide (1.0 g, 1.3 mmol) in pyridine (50 mL) was added benzoyl chloride (0.5 mL, 4.3 mmol, ~2.6 eq) dropwise at 0° C. under argon followed by DMAP (~30 mg). The reaction mixture was stirred at RT overnight and TLC (10/0.75, DCM/MeOH) monitoring showed the formation of monosubstituted (Rf 0.4) and disubstituted (Rf 0.75) products as well as the starting material (Rf 0.12). The solvent was removed in vacuum and the residue was diluted by chloroform. The organic phase was washed with water and dried with anhydrous $Na_2SO_4$. After evaporation of the solvent, the residue was subject to a silica gel column (10/0.75, $CH_2Cl_2$/MeOH) to give the title product 248 mg (yield 22.5%) as a red powder. At the same time, a disubstituted fraction was also obtained and further monodebenzoylation was carried out according to the following: disubstituted compound was dissolved in 20 mL DCM/MeOH (10/1 v/v), then a solution of 2 M MeONa/MeOH was added dropwise to reach pH ~10. After 5 minutes of stirring, Amberlite IR-120 (H$^+$) was added to quench the reaction (pH~7). The reaction mixture was filtered and the filtrate was collected, concentrated, and subjected to a silica-gel column (10/0.75, $CH_2Cl_2$/MeOH) to give the product 100 mg (yield 9%), total yield 31.5% based on starting materials. $^1$H-NMR (25 mg/0.5 mL; CDCl$_3$) δ8.32 (d, 4H, J=8.1 Hz, perylene ring), 8.08 (d, 4H, J=8.1 Hz, perylene ring), 7.98–7.95 (m, 2H, benzene ring), 7.53–7.48 (m, 1H, benzene ring), 7.40–7.35 (m, 2H, benzene ring), 4.45–4.38 (m, 6H, 2CH$_2$N, CH$_2$OBz), 3.91–3.56 (m, 26H, CH2OCH2, HOCH$_2$); $^{13}$C-NMR (60 mg/0.5 mL; CDCl$_3$) δ166.6, 163.04, 162.99, 133.8, 133.1, 130.9, 130.1, 129.8, 128.8, 128.5, 125.5, 122.95, 122.92, 122.8, 72.8, 71.0, 70.9, 70.6, 70.37, 70.33, 69.4, 68.2, 68.1, 64.39, 62.0, 39.6. MS (MALDI): m/z 847.42 [M+H]$^+$, 869.37 [M+Na]$^+$. Anal. Calcd. for C$_{47}$H$_{46}$N$_2$O$_{13}$ (846.87): C, 66.66; H, 5.47; N, 3.31. Found: C, 66.28; H, 5.29; N, 3.48.

Example 6

This example describes the monotritylation of bis-N,N'-(2-(2-(2-(2-hydroxyethoxy)ethoxy)ethoxy)ethyl) perylenetetracarboxylic diimide. 2-[2-[2-(2-Aminoethoxy)ethoxy]ethoxy]ethyl)perylenetetracarboxylic diimide (730 mg, 0.98 mmol) was dissolved in 50 mL pyridine, followed by addition of DMTrCl (750 mg, 2.22 mmol) and DMAP (~10 mg). The mixture was stirred at RT under argon overnight, and TLC monitoring (10/0.75, DCM/MeOH) showed the formation of monosubstituted (Rf 0.5) and disubstituted (Rf 0.8) products as well as the starting material (Rf 0.12). The solvent was removed in vacuum and the residue was subject to silica-gel column (100/5/1, CH$_2$Cl$_2$/MeOH/pyridine) to give the title product 310 mg (yield 30%) as a red powder. Meanwhile, a disubstituted fraction was also collected and further monodetritylation was carried out according to the following: A detritylation solution was made by mixing ZnCl$_2$ (1.5 g) into 110 mL of CH$_2$Cl$_2$/MeOH (10/1, v/v). Then the disubstituted compound was dissolved by 50 mL of the detritylation solution, and the reaction mixture was monitored by TLC (10/0.75, CH$_2$Cl$_2$/MeOH). Upon the appearance of the spot corresponding to bis-N,N'-(2-(2-(2-(2-hydroxyethoxy)ethoxy)ethoxy)ethyl)perylenetetracarboxylic diimide on the TLC plate, the reaction was quenched by pouring into a saturated aq. NaHCO$_3$ solution. The mixture was extracted by chloroform, and the organic layer was washed with brine, collected, concentrated, dried, and subject to silica-gel column (100/5/1, CH$_2$Cl$_2$/MeOH/pyridine) to give the product 180 mg (yield 17.6%), total yield 47.6% based on the starting untritylated material. The product is stored with a stabilizer diisopropylethylamine under argon at –80° C. $^1$H-NMR (CDCl$_3$) δ8.39 (d, 4H, J=8.1 Hz, perylene ring), 8.15 (d, 4H, J=8.1 Hz, perylene ring), 7.44–7.42 (m, 2H, benzene ring), 7.32–7.13 (m, 3H, benzene ring), 7.30 (d, 4H, J=9.0 Hz, methoxylbenzene ring), 6.77 (d, 4H, J=9.0 Hz, methoxylbenzene ring), 4.48–4.39 (m, 4H, 2CH$_2$N), 3.91–3.54 (m, 32H, CH$_3$O, CH$_2$OCH$_2$, HOCH$_2$), 3.17 (t, 2H, J=5.1 Hz, DMTrOCH$_2$). Anal. calcd. for C$_{61}$H$_{60}$N$_2$O$_{14}$ (1045.13): C, 70.10; H, 5.79; N, 2.68. Found: C, 69.66; H, 5.55; N, 3.01.

Example 7

This example describes the preparation of the phosphoramidite of monotritylated bis-N,N'-(2-(2-(2-(2-hydroxyethoxy)ethoxy)ethoxy)ethyl) perylenetetracarboxylic diimide from the product of Example 6. To a solution of monotritylated bis-N,N'-(2-(2-(2-(2-hydroxyethoxy)ethoxy)ethoxy)ethyl) perylenetetracarboxylic diimide (360 mg, 0.34 mmol) in 25-mL CH$_2$Cl$_2$ (dry) was added 0.25 mL (~4 eq) diisopropylethylamine. Then chloro-N,N-diisopropylaminocyanoethoxyphosphane (0.1 mL, 0.45 mmol, ~1.3 eq) was added dropwise at RT under argon. After 20 min of stirring under argon at RT, the reaction mixture was diluted with CH$_2$Cl$_2$/Et$_3$N (300/15, v/v) 100 mL, and the organic phase was washed with a saturated aq. NaHCO$_3$ solution and brine. The organic layer was dried over Na$_2$SO$_4$, filtered, and evaporated to dryness. The residue was subject to a silica-gel column (CH$_2$Cl$_2$/EtOAc/Et$_3$N, 3/6/1) to give the title product 386 mg (yield 90%) as a red powder, which should be used freshly for the next phosphotriester step in order to achieve a higher coupling yield. $^1$H-NMR (CDCl$_3$) δ8.42 (d, 2H, J=3.6 Hz, perylene ring), 8.39 (d, 2H, J=3.6 Hz, perylene ring), 8.19 (d, 2H, J=3.0 Hz, perylene ring), 8.17 (d, 2H, J=3.0 Hz, perylene ring), 7.45–7.41 (m, 2H, benzene ring), 7.30 (dt, 4H, J=2.4, 9.3 Hz, methoxylbenzene ring), 7.28–7.12 (m, 3H, benzene ring), 6.77 (dt, 4H, J=2.1, 9.0 Hz, methoxylbenzene ring), 4.44 (bt, 4H, 2CH$_2$N), 3.89–3.58 (m, 34H, CH$_3$O, CH$_2$OCH$_2$, ((CH$_3$)$_2$CH)$_2$NP (OCH$_2$CH$_2$CN)(OCH$_2$), 3.17 (t, 2H, J=5.1 Hz, DMTrOCH$_2$), 2.64 (bt, 2H, OCH$_2$CH$_2$CN), 1.18 (d, 6H, J=5.4 Hz, (CH$_3$)$_2$CH). $^{31}$P-NMR (CDCl$_3$) δ149.44 (s).

Example 8

This example describes the preparation of DMTr-protected monobenzoylated dimer (2-DMTr). The phosphoramidite produced in Example 7 (616 mg, 0.5 mmol) and the monobenzoylated anchor produced according to Example 5 (200 mg, 0.24 mmol) were dried at RT in high vacuum for 24 hrs. and dissolved in dry CH$_2$Cl$_2$ (30 mL). 3 Å MS (0.5 g) was added into the solution, and the mixture was stirred for 15 min under argon. Then N-PhIMT (215 mg, 0.73 mmol) was added into the mixture. After 5 hrs. of stirring at RT under argon, a 0.2 M solution of I$_2$ (5 mL of CH$_2$Cl$_2$/Pyridine/H$_2$O, 1/3/1, v/v/v) was added dropwise into the reaction. The mixture was stirred for 20 min, then filtered, and the residue was washed with chloroform. The filtrate was washed with a 5% Na$_2$S$_2$O$_3$ aq. solution and brine, and extracted with chloroform. The organic layer was dried over Na$_2$SO$_4$, filtered, and evaporated to dryness. The residue was subjected to silica-gel column chromatography (CH$_2$Cl$_2$/MeOH/pyridine, 400/30/2) to give the crude title product, which was typically carried to the next step—detritylation. $^1$H-NMR (CDCl$_3$) δ8.16 (d, 4H, J=8.1 Hz, perylene ring), 8.13 (d, 4H, J=7.8 Hz, perylene ring), 7.89–7.84 (m, 2H, benzoyl ring), 7.85–7.80 (m, 8H, perylene ring), 7.46–7.13 (m, 8H, benzoyl and benzene ring), 7.30 (d, 4H, J=9.0 Hz, methoxylbenzene ring), 6.77 (dt, 4H, J=2.1, 9.0 Hz, methoxylbenzene ring), 4.42–4.20 (m, 16H, 4CH$_2$N, CH$_2$OBz, O=P(OCH$_2$—)$_2$ (OCH$_2$CH$_2$CN)), 3.92–3.56 (m, 54H, CH$_3$O, CH$_2$OCH$_2$), 3.17 (t, 2H, J=5.1 Hz, DMTrOCH$_2$), 2.89 (t, 2H, J=6.9 Hz, OCH$_2$CH$_2$CN).

Example 9

The example describes the detritylation of the product produced according to Example 8, to produce the monobenzoylated dimer compound. The crude tritylated dimer from Example 8 was dissolved in CH$_2$Cl$_2$ 30 mL, and 1 mL of Cl$_2$CHCOOH was added into the solution dropwise at RT. After 10 min of stirring, chloroform was added to dilute the reaction mixture, and the organic phase was washed with a saturated NaHCO$_3$ solution and brine. The organic layer was dried over Na$_2$SO$_4$, filtered, and evaporated to dryness. The residue was subject to a silica-gel column (CH$_2$Cl$_2$/MeOH, 400/30) to give the title product (275 mg, 67% two steps) as a red powder. $^1$H-NMR (10 mg/0.5 mL; CDCl$_3$) δ8.19 (d, 2H, J=8.1 Hz, perylene ring), 8.18 (d, 2H, J=8.1 Hz, perylene ring), 8.15 (d, 2H, J=8.1 Hz, perylene ring), 8.14 (d, 2H, J=7.8 Hz, perylene ring), 7.97–7.94 (m, 2H, benzoyl ring), 7.88–7.82 (m, 8H, perylene ring), 7.53–7.46 (m, 1H, benzoyl ring), 7.39–7.34 (m, 2H, benzoyl ring), 4.42–4.20 (m, 16H, 4CH$_2$N, CH$_2$OBz, O=P(OCH$_2$—)$_2$ (OCH$_2$CH$_2$CN)), 3.91–3.56 (m, 50H, CH$_2$OCH$_2$), 2.89 (t, 2H, J=6.0 Hz, OCH$_2$CH$_2$CN). $^{13}$C-NMR (60 mg/0.5 mL; CDCl$_3$) δ166.6, 162.71, 162.67, 162.64, 133.23, 133.16, 133.14, 130.51, 130.14, 129.77, 128.47, 128.32, 128.27, 124.94, 124.88, 122.64, 122.55, 117.47, 77.52, 72.85, 70.93, 70.89, 70.59, 70.38, 70.34, 70.30, 70.23, 70.15, 69.43, 68.18, 68.15, 68.09, 67.61, 67.53, 64.41, 62.49, 62.42, 61.99, 39.60, 20.01, 19.91. $^{31}$P-NMR (CDCl$_3$) δ-0.52 (s). MS (MALDI): m/z 1705.33 [M+H]$^+$, 1726.82 [M+Na]$^+$, 1749.39 [M+2Na–H]$^+$.

Example 10

This example describes the preparation of DMTr-protected monobenzoylated trimer (3-DMTr) from the phosphoramidite building block prepared in Example 7 (386 mg, 0.31 mmol) and monobenzoylated dimer prepared according to Example 9 (171 mg, 0.1 mmol). The starting materials were dried at RT in high vacuum for 24 hrs. and dissolved in dry CH$_2$Cl$_2$ (30 mL). 3 Å MS (0.5 g) was added into the solution and the mixture was stirred for 15 min under argon. Then N-PhIMT (120 mg, 0.34 mmol) was added into the mixture. After 5 hrs of stirring at RT under argon, a 0.2 M solution of I$_2$ (5 mL of CH$_2$Cl$_2$/pyridine/H$_2$O, 1/3/1, v/v/v) was added dropwise into the reaction. The mixture was stirred for 20 min, then filtered and the residue was washed with chloroform. Following the workup procedure described for the synthesis of 2-DMTr (Example 8), after the column chromatography, we obtained 3-DMTr, which was directly proceeded to the next step—detritylation. $^1$H-NMR (CDCl$_3$) δ8.06–7.92 (m, 14H, perylene ring and benzoyl ring), 7.67–7.63 (m, 8H, perylene ring), 7.55–7.15 (m, 16H, perylene ring, benzene ring, benzoyl ring, methoxylbenzene ring), 6.79–6.75 (m, 4H, methoxylbenzene ring), 4.41–4.20 (m, 26H, CH$_2$N, CH$_2$OBz, O=P(OCH$_2$-)$_2$(OCH$_2$CH$_2$CN)), 3.94–3.58 (m, 78H, OCH$_3$, CH$_2$OCH$_2$), 3.18 (t, 2H, J=5.1 Hz, CH$_2$ODMTr), 2.89 (t, 4H, J=7.0 Hz, OCH$_2$CH$_2$CN).

Example 11

This example describes the preparation of a monobenzoylated trimer via detritylation. The crude product of Example 10 was dissolved in 20 mL CH$_2$Cl$_2$, and 0.6 mL of Cl$_2$CHCOOH was added into the solution dropwise at RT. After 10 min of stirring, chloroform was added to dilute the reaction mixture, and the organic phase was washed with a saturated NaHCO$_3$ solution and brine. The organic layer was dried over Na$_2$SO$_4$, filtered, and evaporated to dryness. The residue was subject to a silica-gel column (CH$_2$Cl$_2$/MeOH, 400/40–400/50) to give the title product 3 (200 mg, 78% two steps) as a red powder. $^1$H-NMR (5 mg/0.5 mL; CDCl$_3$) δ8.12 (d, 2H, J=8.1 Hz, perylene ring), 8.11 (d, 2H, J=8.1 Hz, perylene ring), 8.08 (d, 2H, J=8.1 Hz, perylene ring), 8.07 (d, 2H, J=7.8 Hz, perylene ring), 8.03 (2d, 4H, J=7.8 Hz, perylene ring), 7.97–7.93 (m, 2H, benzoyl ring), 7.79–7.74 (4d, 8H, J=7.8, 8.1 Hz, perylene ring), 7.66 (bd, 4H, perylene ring), 7.53–7.46 (m, 1H, benzoyl ring), 7.39–7.33 (m, 2H, benzoyl ring), 4.41–4.22 (m, 26H, CH$_2$N, CH$_2$OBz, O=P(OCH$_2$—)$_2$(OCH$_2$CH$_2$CN)), 3.92–3.56 (m, 72H, CH$_2$OCH$_2$), 2.92 (bt, 4H, J=6.2 Hz, OCH$_2$CH$_2$CN). $^{13}$C-NMR (35 mg/0.5 ml; CDCl$_3$) δ166.6, 162.56, 162.54, 162.48, 162.42, 133.14, 133.01, 132.90, 132.76, 130.34, 130.20, 130.14, 129.77, 128.48, 128.11, 128.06, 128.01, 127.90, 124.73, 124.59, 124.45, 122.49, 122.41, 122.38, 122.32, 117.56, 77.53, 72.84, 70.93, 70.89, 70.61, 70.36, 70.25, 70.16, 69.44, 68.11, 67.62, 67.55, 64.41, 62.53, 62.46, 61.99, 39.55, 20.02, 19.93. $^{31}$P-NMR (CDCl$_3$) δ-0.49 (s). MS (MALDI): m/z 2563.41 [M+H]$^+$, 2584.94 [M+Na]$^+$, 2607.52 [M+2Na—H]$^+$.

Example 12

This example describes the preparation of a DMTr-protected monobenzoylated tetramer (4-DMTr) via coupling of the trimer of Example 11 to the phosphoramidite building block of Example 7. The phosphoramidite (386 mg, 0.31 mmol) and monobenzoylated trimer (166 mg, 0.065 mmol) were dried at RT in high vacuum for 24 hrs and dissolved in dry DCM (30 mL). 3 Å MS (0.5 g) was added into the solution and the mixture was stirred for 15 min under argon. Then, N-PhIMT (120 mg, 0.34 mmol) was added into the mixture. After 5 hrs. of stirring at RT under argon, a 0.2 M solution of I$_2$ (5 mL of CH$_2$Cl$_2$/pyridine/H$_2$O, 1/3/1, v/v/v) was added dropwise into the reaction. The mixture was stirred for 20 min, then filtered, and the residue was washed with chloroform. Following the workup procedure described for the synthesis of 2-DMTr, after the column chromatography, the title product 4-DMTr was obtained as a crude product, which was directly proceeded to the next step—detritylation. $^1$H-NMR (CDCl$_3$) δ8.06–7.87 (m, 18H, perylene ring and benzoyl ring), 7.69–7.61 (m, 8H, perylene ring), 7.55–7.15 (m, 20H, perylene ring, benzene ring, benzoyl ring, methoxylbenzene ring), 6.79–6.75 (m, 4H, methoxylbenzene ring), 4.42–4.15 (m, 36H, CH$_2$N, CH$_2$OBz, O=P(OCH$_2$—)$_2$(OCH$_2$CH$_2$CN)), 3.94–3.55 (m, 102H, OCH$_3$, CH$_2$OCH$_2$), 3.18 (t, 2H, J=5.1 Hz, CH$_2$ODMTr), 2.98–2.89 (m, 6H, OCH$_2$CH$_2$CN).

Example 13

This example describes the detritylation of the tetramer produced according to Example 12 to give the corresponding monobenzoy protected tetramer. The crude tetramer was dissolved in 20-mL CH$_2$Cl$_2$, and 0.6 mL of Cl$_2$CHCOOH was added into the solution dropwise at RT. After 10 min of stirring, chloroform was added to dilute the reaction mixture, and the organic phase was washed with a saturated NaHCO$_3$ solution and brine. The organic layer was dried over Na$_2$SO$_4$, filtered, and evaporated to dryness. The residue was subject to a silica-gel column (CH$_2$Cl$_2$/MeOH, 400/40–400/50) to give the product (180 mg, 81% two steps) as a red powder. $^1$H-NMR (30 mg/0.5 mL; CDCl$_3$) δ7.97–7.93 (m, 2H, benzoyl ring), 7.89–7.70 (8d, 16H, J=7.8 Hz, perylene ring), 7.53–7.20 (m, 19H, benzoyl ring and perylene ring), 4.44–4.14 (m, 36H, CH$_2$N, CH$_2$OBz, O=P(OCH$_2$—)$_2$(OCH$_2$CH$_2$CN)), 3.90–3.56 (m, 96H, CH$_2$OCH$_2$), 2.97–2.89 (3t, 6H, J=6 Hz, OCH$_2$CH$_2$CN). $^{13}$C-NMR (30 mg/0.5 mL; CDCl$_3$) δ 166.6, 162.55, 162.51, 162.45, 162.36, 133.14, 132.99, 132.86, 132.66, 130.34, 130.27, 130.14, 129.77, 128.49, 128.11, 128.06, 127.96, 127.82, 124.70, 124.55, 124.36, 124.33, 122.47, 122.38, 122.34, 122.26, 117.63, 117.58, 117.56, 77.52, 72.84, 70.93, 70.89, 70.61, 70.36, 70.26, 70.17, 69.44, 68.10, 67.63, 67.55, 64.41, 62.54, 62.47, 61.99, 39.55, 30.04, 20.03, 19.93. $^{31}$P-NMR (CDCl$_3$) δ-0.51 (s). MS (MALDI): m/z 3421.98 [M+H]$^+$, 3443.76 [M+Na]$^+$, 3466.17 [M+2Na—H]$^+$.

Example 14

This example describes the preparation of a DMTr-protected monobenzoylated pentamer (5-DMTr) via coupling of the tetramer of Example 13 to the phosphoramidite building block of Example 7. The phosphoramidite (290 mg, 0.23 mmol) and monobenzoylated tetramer (100 mg, 0.03 mmol) were dried at RT in high vacuum for 24 hrs and dissolved in dry $CH_2Cl_2$ (20 mL). 3 Å MS (0.5 g) was added to the solution, and the mixture was stirred for 15 min under argon. Then N-PHIMT (80 mg, 0.27 mmol) was added into the mixture. After 5 hrs of stirring at RT under argon, a 0.2 M solution of $I_2$ (3 mL of $CH_2Cl_2$/pyridine/$H_2O$, 1/3/1, v/v/v) was added dropwise into the reaction. The mixture was stirred for 20 min, then filtered, and the residue was washed with chloroform. Following the workup procedure described for the synthesis of 2-DMTr, after the column chromatography, 5-DMTr was obtained as a crude product, which was directly proceeded to the next step—detritylation. $^1$H-NMR ($CDCl_3$) δ7.96–7.93 (m, 2H, benzoyl ring), 7.88–7.56 (m, 20H, perylene ring), 7.54–7.04 (m, 32H, perylene ring, benzene ring, benzoyl ring, methoxylbenzene ring), 7.76 (d, 4H, J=8.7 Hz, methoxylbenzene ring), 4.42–4.12 (m, 46H, $CH_2N$, $CH_2OBz$, O=P($OCH_2$—)$_2$($OCH_2CH_2CN$)), 3.86–3.54 (m, 126H, $OCH_3$, $CH_2OCH_2$), 3.16 (t, 2H, J=5.1 Hz, $CH_2ODMTr$), 2.96–2.88 (4t, 8H, J=6 Hz, $OCH_2CH_2CN$).

Example 15

This example describes the preparation of the monobenzoylated pentamer via detritylation of the product of Example 14. The crude 5-DMTr was dissolved in 20 mL $CH_2Cl_2$, and 0.6 mL of $Cl_2CHCOOH$ was added into the solution dropwise at RT. After 10 min of stirring, chloroform was added to dilute the reaction mixture, and the organic phase was washed with a saturated $NaHCO_3$ solution and brine. The organic layer was dried over $Na_2SO_4$, filtered, and evaporated to dryness. The residue was subject to a silica-gel column ($CH_2Cl_2$/MeOH, 400/60) to give the pentamer (87 mg, 68% two steps) as a red powder. $^1$H-NMR (20 mg/0.5 mL; $CDCl_3$) δ7.99–7.95 (m, 2H, benzoyl ring), 7.94–7.79 (4d, 8H, J=7.8 Hz, perylene ring), 7.78–7.68 (m, 12H, perylene ring), 7.55–7.20 (m, 23H, benzoyl ring and perylene ring), 4.44–4.16 (m, 46H, $CH_2N$, $CH_2OBz$, O=P($OCH_2$—)$_2$($OCH_2CH_2CN$)), 3.90–3.58 (m, 120H, $CH_2OCH_2$), 2.98–2.89 (4t, 8H, J=6.6 Hz, $OCH_2CH_2CN$). $^{13}$C-NMR (50 mg/0.5 mL; $CDCl_3$/MeOH 10/1 v/v) δ166.8, 162.62, 162.61, 162.57, 162.51, 162.42, 162.41, 133.18, 133.00, 132.94, 132.89, 132.67, 132.57, 130.34, 130.32, 130.12, 130.11, 129.92, 129.66, 128.45, 127.96, 127.95, 127.94, 127.93, 127.70, 124.61, 124.51, 124.27, 124.17, 122.51, 122.38, 122.28, 122.16, 122.05, 117.54, 117.49, 77.59, 72.82, 70.74, 70.26, 70.10, 70.01, 69.31, 67.94, 67.68, 67.61, 64.37, 62.62, 62.57, 61.50, 39.47, 29.94, 19.86, 19.77. $^{31}$P-NMR ($CDCl_3$) δ-0.51 (s). MS (MALDI): m/z 4301.80 $[M+Na]^+$, 4323.62 $[M+2Na—H]^+$.

Example 16

This example describes the production of DMTr-protected monobenzoylated hexamer (6-DMTr) via coupling of the pentamer produced in Example 15 with the phosphoramidite building block of Example 7. The phosphoramidite (180 mg, 0.14 mmol) and monobenzoylated pentamer (60 mg, 0.014 mmol) were dried at RT in high vacuum for 24 hours, and dissolved in dry $CH_2Cl_2$ (20 mL). 3 Å MS (0.2 g) was added into the solution, and the mixture was stirred for 15 min under argon. Then, N-PhIMT (50 mg, 0.17 mmol) was added into the mixture. After 5 h of stirring at RT under argon, a 0.2 M solution of $I_2$ (2 mL of $CH_2Cl_2$/pyridine/$H_2O$, 1/3/1, v/v/v) was added dropwise into the reaction. The mixture was stirred for 20 min, then filtered, and the residue was washed with chloroform. Following the workup procedure described for the synthesis of 2-DMTr, after the column chromatography, 6-DMTr was obtained as a crude product, which was directly proceeded to the next step—detritylation. $^1$H-NMR ($CDCl_3$) δ7.98–7.93 (m, 2H, benzoyl ring), 7.89–7.55 (m, 24H, perylene ring), 7.53–7.45 (m, 1H, benzoyl ring), 7.45–7.04 (m, 35H, perylene ring, benzene ring, benzoyl ring, methoxylbenzene ring), 7.76 (dt, 4H, J=2.0, 8.7 Hz, methoxylbenzene ring), 4.42–4.12 (m, 56H, $CH_2N$, $CH_2OBz$, O=P($OCH_2$—)$_2$($OCH_2CH_2CN$)), 3.86–3.55 (m, 150H, $OCH_3$, $CH_2OCH_2$), 3.16 (t, 2H, J=5.1 Hz, $CH_2ODMTr$), 2.96–2.88 (5t, 10H, J=6.3 Hz, $OCH_2CH_2CN$).

Example 17

This example describes the synthesis of the monobenzoylated hexamer from the product of Example 16 via detritylation. The crude 6-DMTr was dissolved in 20 mL $CH_2Cl_2$, and 0.6 mL of $Cl_2CHCOOH$ was added into the solution dropwise at RT. After 15 min of stirring, chloroform was added to dilute the reaction mixture, and the organic phase was washed with a saturated $NaHCO_3$ solution and brine. The organic layer was dried over $Na_2SO_4$, filtered, and evaporated to dryness. The residue was subject to a silica-gel column ($CH_2Cl_2$/MeOH, 400/80) to give hexamer 6 (55 mg, 77% two steps) as a red powder. $^1$H-NMR (10 mg/0.5 mL; $CDCl_3$) δ7.98–7.94 (m, 2H, benzoyl ring), 7.90–7.73 (4d, 8H, J=7.8, 8.1 Hz, perylene ring), 7.73–7.61 (m, 16H, perylene ring), 7.55–7.10 (m, 27H, benzoyl ring and perylene ring), 4.43–4.14 (m, 56H, $CH_2N$, $CH_2OBz$, O=P($OCH_2$—)$_2$($OCH_2CH_2CN$)), 3.88–3.54 (m, 144H, $CH_2OCH_2$), 2.98–2.88 (5t, 10H, J=6.3 Hz, $OCH_2CH_2CN$). $^{13}$C-NMR (40 mg/0.5 mL; $CDCl_3$) δ 166.6, 162.41, 162.39, 162.30, 162.22, 162.20, 133.16, 132.79, 132.58, 132.45, 132.39, 130.14, 129.96, 129.94, 129.77, 128.50, 127.90, 127.70, 127.53, 124.46, 124.20, 124.04, 124.02, 122.30, 122.18, 122.13, 122.05, 122.02, 117.67, 117.63, 117.60, 77.53, 72.90, 70.86, 70.54, 70.31, 70.25, 70.16, 69.43, 68.01, 67.66, 67.58, 64.42, 62.61, 62.54, 61.91, 39.49, 30.03, 20.02, 19.93. $^{31}$P-NMR ($CDCl_3$) δ-0.54 (s). MS (MALDI): m/z 5158.59 $[M+Na]^+$, 5181.10 $[M+2Na—H]^+$.

Example 18

This example includes the thermodynamic parameters measured for perylene-perylene intramolecular self-association promoted folding (Table 1). The foldable polymers measured in water have the repeating sequence: perylene-tetra(ethylene glycol)-nf-κb DNA-tetra(ethylene glycol)-perylene, whereas the foldable polymers measured in organic solvent have a repeating sequence: perylene-tetra(ethylene glycol)-phosphotriester-tetra(ethylene glycol)-perylene. Replacement of DNA with a phosphotriester group (TEG-O-P($OCH_2CH_2CN$)—O-TEG) confers sufficient solubility in the organic solvent.

TABLE 1

| No. of perylene units in polymer | Organic Solvent ($Cl_2CHCHCl_2$) | | Water | |
|---|---|---|---|---|
| | $\Delta S°$ (cal/mol · K) | $\Delta H°$ (kcal/mol) | $\Delta S°$ (cal/mol · K) | $\Delta H°$ (kcal/mol) |
| 2 | −6.60 ± 0.40 | −3.01 ± 0.06 | 8.64 ± 0.28 | 2.72 ± 0.09 |
| 3 | −15.4 ± 1.4 | −6.62 ± 0.43 | 14.3 ± 0.3 | 4.44 ± 0.09 |

TABLE 1-continued

| No. of perylene units in polymer | Organic Solvent (Cl₂CHCHCl₂) | | Water | |
|---|---|---|---|---|
| | $\Delta S°$ (cal/mol · K) | $\Delta H°$ (kcal/mol) | $\Delta S°$ (cal/mol · K) | $\Delta H°$ (kcal/mol) |
| 4 | −10.7 ± 0.28 | −5.09 ± 0.09 | 15.4 ± 0.3 | 4.78 ± 0.09 |
| 5 | −8.28 ± 0.14 | −4.35 ± 0.04 | 21.7 ± 0.6 | 6.88 ± 0.22 |

Example 19

This example describes the incorporation of chromophore moieties into DNA, using solid-phase synthesis techniques, and using the perylene building blocks prepared, for example, as described in the working embodiments above. Because these chromophoric building blocks include phosphoramidites on primary alcohol groups, their reactivity is much higher than the same phosphoramidite on the secondary hydroxyl groups of the normal DNA bases (A, T, C, and G). Therefore, the chromophoric phosphoramidite should be synthesized fresh each time and should be used immediately after each synthesis.

The hybrid DNA-perylene sequences were synthesised on solid supports using an automated DNA synthesizer (Applied Biosystem 8909). The typical coupling yield of the chromophore to any DNA bases was ~100%. The reverse coupling of DNA to the chromophore was also 100%. In order to achieve such high coupling, the default commercial DNA synthesis protocols were reprogrammed. Using the original protocol resulted in poor yield (~20%). Specifically, the protocol was modified to increase the reaction time from 94 seconds to 210 seconds per monomer coupling. Typically, the coupling step also was repeated 10 times before capping and oxidization steps. This modified protocol ensures essentially quantitative yield between the DNA base and the chromophoric building block.

Example 20

This example describes the purification of the synthesized probes using polyacrylamide gels to yield foldable polymers having single-molecular-weight distributions. Before optimization of the DNA synthetic protocol, each addition of the rigid conjugated unit caused a fraction of the hybrid polymer chains to terminate, accounting for the formation of polymers consisting of perylene dimer, trimer, tetramer, and pentamer. Single-molecular-weight distributions of these natural-synthetic foldable polymers were easily separated on polyacrylamide gels (not shown). Foldable polymers with single-molecular-weight distributions were separated by cutting out the gel fraction, followed by extraction of the hybrid polymer with an elution buffer (500 mM NH₄Ac, 10 mM MgAc₂, 1 mM EDTA, 0.1% SDS). These polymers were easily visualized on the gel because the perylene tetracarboxylic diimide imparted a pink colour. Since the larger polymers migrated more slowly, the upper bands were from polymers with five perylene units. The first two lines observed were due to two polymers containing five perylene units that differed in the lengths of their perylene tails. The third, fourth, and fifth strong lines indicated the location of foldable polymer with, four, three, and two perylene units, respectively.

Gel preparation: 37.5 g of urea, 7.5 mL of TBE buffer (1.0 M Tris-borate (pH 8.3), 20 mM EDTA), and 15 mL 40% acrylamide/bis 29:1 solution were nuxed in a flask with distilled water to a final volume of 75 mL (gentle heating to promote quick dissolution of urea). The above solution was degassed in vacuum, followed by addition of 25 μL tetramethyl ethylene diamine (TEMED) and 525 μL 10% ammonium persulfate prior to gel casting. After addition of polymerization initiators, the solution was then casted into a gel using a Bio-Rad integral plate chamber (size: 21×40 cm, spacers: 0.75 mm). The upper buffer chamber was filled with 350–500 mL of running buffer (1×TBE), the lower chamber with 400 mL of running buffer (1×TBE). Prior to sample loading, the gel was pre-run and its temperature was brought to 50° C. The gel temperature was never allowed to exceed 60° C. under any circumstance to avoid overheating.

Electrophoresis: The sample was mixed with loading buffer and loaded carefully onto the gel (2–3 OD per cm.). The gel was run with constant power of 45 W, while keeping the temperature at 50° C., until the bromophenol blue migrated to the bottom of the plate.

Foldable polymer elution: The top glass plate was removed, the desired pink color bands were carefully cut out with a razor blade and transferred into a sterile plastic tube. The gel was then chopped into small pieces, and sufficient elution buffer (500 mM ammonium acetate, 10 mM magnesium acetate, 1 mM EDTA, 0.1% SDS) was added to extract the hybrid polymers. The extraction mixture was then sealed and incubated at 37° C. for 6 hrs. The solution containing foldable polymer was separated from the gel fragments by 5-min centrifugation at 13.2 rpm. The clear elution solution was removed and another 500 μL of elution buffer was added to the gel fragments to extract foldable polymers again for 30 min at 60° C. The aqueous extracts were combined and equilibrated with n-butanol three times to remove sodium dodecyl sulfate (SDS) from the aqueous layer. To the final aqueous solution was added 3M sodium acetate and absolute ethanol. The volume of sodium acetate added was one-tenth of the volume of the aqueous hybrid polymer solution and the volume of ethanol added was three times of the volume of the aqueous hybrid polymer solution. The mixture was inverted a couple times to ensure complete mixing and chilled at −70° C. for 30 min to precipitate the hybrid polymers. Pure hybrid polymers were obtained after centrifugation at 13.2 rpm for 10 min.

Example 21

This example describes the template directed ligation of two DNA oligonucleotides attached to opposite ends of an "accordion" comprising three chromophore moieties. The change in the interactions of the chromophore moieties upon ligation was observed via fluorescent emissions and allows the monitoring of the ligation. In this example, the 5'-end of the single-strand DNA of an "accordion" probe had two blue emitters (OPV-1) sandwiching a red emitter (DAP-1).

The three-chromophore probe had a thirty base DNA oligonucleotide on either side; sequences of these two strings are complementary to two contiguous regions at the multiple cloning site (MSC) of bacteriophage M13 (mp18). The sequence on the 5'-end of the probe was 5'-CATGCC-TGCAGG-TCGACT-CTAGAG-GATCCC-accordion, (SEQ ID NO: 5) whereas the sequence on the 3'-end of the accordion was accordion-TCATAG-CTGTTT-CCTGTG-TGAAAT-TGTTAT-3' (SEQ ID NO: 6). The total synthesis of the probe was successfully completed on a solid-phase synthesizer with high yields. The accordion is linked to the DNA blocks via tetra(ethylene glycol) ("TEG") and the linkage between two chromophores is two TEG moieties connected by a phosphate group.

First, the 5'-end of the single-strand DNA of the probe was phosphorylated with T4 polynucleotide kinase in a ligase buffer (66 mM Tris-HCl, 10 mM $MgCl_2$, 1 mM dithiothreitol, 1 mM ATP, 7.5% polyethylene glycol or PEG 6000) at a pH value of 7.6. Then a complementary single-strand DNA, was added to bring the 5'-end and 3'-end of the probe DNA into ajuxtaposed position (See, FIG. 9). The sequence of the 60 bases was 5'-GGGATC-CTCTAG-AGTCGA-CCTGCA-GGCATG-ATAACA-ATTTCA-CACAGG-AAACAG-CTATGA-3'. Hybridization brought the accordion macromolecule into a circle consisting of three chromophores linked by foldable TEG hinges and a double-strand DNA with a nick in the middle. The nick in the duplex DNA provides flexibility and allowed the chromophores to stack.

The nick was then ligated as follows: to the complex formed between molecular accordion and single-strand DNA, T4 quick ligase was added with the ligase buffer. The reaction mixture was incubated at 37° C. for a few hours. The reaction mixture and blank reference sample (no kinase/ligase treatments) were dotted on a microscope slide and their respective fluorescences were viewed on an UV-illuminator. The enzymes-treated (kinase/ligase) mixture emitted bright blue, whereas the blank reference sample emitted pink color.

These results demonstrated that the enzymes (kinase and ligase) repaired the DNA nick in the accordion complex. As a result the flexibility of the hinge in the double strand DNA was replaced with a rigid DNA duplex. In the rigid DNA duplex the accordion was stretched and could only adopt an extended form. In this conformation, fluorescence-energy transfer was at minimum; when the accordion was excited at 365 nm, only blue photons were observed. In the blank reference sample, the nick in double-strand DNA functioned as a hinge and allowed the accordion to form stacked structures. Consequently, its spot emitted a pink color when excited at 365 nm due to FRET from blue chromophores to the red chromophore. Note that these fluorescence colors were produced from dried spots. Both solutions emitted blue color.

Nick repair ligation also was detected with two other probes having the same DNA sequence but different chromophores. The first probe contained OPV-1, DAP-1, OPV-1 and existed in a stretched configuration in water; the second probe contained HPTD-HPTD-HPTD and existed as a tightly folded conformation in water.

Example 22

This example describes the preparation of 2-(2-(2-(2-chloroethoxy)ethoxy)ethoxy)ethanol. A mixture of tetraethylene glycol (40 g, 0.2 mol), dry $CHCl_3$ (50 mL), and dry pyridine (17 mL) was cooled to 0° C., and $SOCl_2$ (15 mL, 0.2 mol) was added during 1.5 h, keeping the reaction temperature below 10° C. under argon. The temperature was then raised to 60° C. Stirring and heating were continued for 24 h under argon. After cooling the reaction mixture to room temperature, the solvents were evaporated in vacuum and the residue was mixed with water (100 mL). The aqueous solution was washed with hexane (2×100 mL), and the crude product was extracted into toluene (10×100 mL). The toluene extracts were dried with $MgSO_4$ before the solvent was evaporated. The residue was subject to silica gel column using the gradient elution technique with EtOAc/hexane (80:20 to 100:0) to afforded 2-(2-(2-(2-chloroethoxy)ethoxy)ethoxy)ethanol as a colorless liquid (9 g, 21%). $^1$H NMR ($CDCl_3$) δ (ppm): 3.76–3.56 (m, 16H), 2.62 (s, 1H); $^{13}$C NMR ($CDCl_3$) δ (ppm): 72.6, 71.5, 70.8, 70.8, 70.7, 70.5, 61.9, 42.9. Analytical data matched that reported by Amabilino et al. *J. Am. Chem. Soc.* 117, 1271–1293, 1995.

Example 23

This example describes the preparation of a precursor to E,E-1,4-Bis-4,4'-(2-(2-(2-(2-hydroxyethoxy)ethoxy)ethoxy)ethoxy)styryl benzene: 4-[2-[2-[2-(2-hydroxyethoxy)ethoxy]ethoxy]ethoxy]-benzaldehyde. A mixture of 2-(2-(2-(2-chloroethoxy)ethoxy)ethoxy)ethanol (2.0 g, 9.4 mmol), 4-hydroxybenzaldehyde (1.4 g, 1.2 equal), and $K_2CO_3$ (2.5 g, 2 equal) in dry N,N-dimethylformamide (DMF) (10 mL) was heated to 100° C. (oil bath 110° C.) under argon. The stirring was continued at this temperature for 72 hrs. After the reaction mixture was cooled to room temperature, the solvent (DMF) was evaporated in vacuum and the residue was diluted with $CHCl_3$. The obtained suspension was suction-filtered and the filtrate was collected. After drying over $Na_2SO_4$, the organic phase was concentrated and the residue was purified by chromatography on a silica gel column eluted with EtOAc/MeOH (20:1) to give the title product (2.25 g, yield 80%) as a yellow oil: $R_f$0.3 (EtOAc/MeOH 20/1). $^1$H NMR ($CDCl_3$) δ (ppm): 9.87 (s, 1H, —CHO), 7.82 (dt, 2H, $J_1$=9.0 Hz, $J_2$=2.7 Hz, benzene ring), 7.01 (dt, 2H, J=9.0 Hz, $J_2$=2.7 Hz, benzene ring), 4.22 (bt, 2H, J=4.8 Hz, tetraethylene glycol chain), 3.89 (bt, 2H, J=4.8 Hz, tetraethylene glycol chain), 3.77–3.59 (m, 12H, tetraethylene glycol chain), 2.53 (t, 1H, J=6.0 Hz, —OH); $^{13}$C NMR ($CDCl_3$) δ (ppm): 190.9, 163.9, 132.1, 130.1, 115.0, 72.65, 71.07, 70.86, 70.78, 70.53, 69.68, 67.92, 61.95.

Example 24

This example describes the preparation of E,E-1,4-Bis-4,4'-(2-(2-(2-(2-hydroxyethoxy)ethoxy)ethoxy)ethoxy)styryl benzene. A mixture of tetraethyl 1,4-xylylenediphosphonate (1.05 g, 2.78 mmol) (this Homer-Wadsworth-Emmons reagent, tetraethyl 1,4-xylylenediphosphonate, was obtained according the procedures of Stuhr-Hansen et al. *J. Org. Chem.*, 68(4):1275–1282, 2003; and of Schwöppe and Meier *J. Prakt. Chem.* 342:459, 2000) and 3 equivalent of 4-[2-[2-[2-(2-hydroxyethoxy)ethoxy]ethoxy]ethoxy]-benzaldehyde (2.45 g, 8.22 mmol) was dried in vacuum overnight and dissolved in anhydrous DMF (25 mL) under argon. To the stirred solution of bisphosphonate and aldehyde at 0° C. was added dropwise a solution of potassium tert-butoxide (KOtBu) (922 mg, 3 equal) in anhydrous DMF (15 mL) over 15 min by syringe. After stirring for 0.5 h at 0° C., the reaction mixture was slowly warmed up to room temperature and stirred for another 12 h, the reaction was quenched with water. The crude product was collected by suction filtration and the filtrate was evaporated to dryness. The residue was resolved with $CHCl_3$ and washed with water (2×100 mL). The organic layer was dried over $Na_2SO_4$ and concentrated to dryness. The crude product was then purified by being washed with tetrahydrofuran (THF) twice to give 1.69 g (91%) of the title compound. $^1$H NMR ($CDCl_3$) δ (ppm): 7.47 (s, 4H, aromatic ring), 7.45 (d, 4H, J=8.7 Hz, aromatic ring), 7.06 (d, 2H, J=16.2 Hz, double bond trans-linkage), 6.97 (d, 2H, J=16.2 Hz, double bond trans-linkage), 6.92 (d, 4H, J=8.7 Hz, aromatic ring), 4.16 (bt, 4H, J=4.8 Hz, tetraethylene glycol chain), 3.87 (bt, 4H, J=4.8

Hz, tetraethylene glycol chain), 3.78–3.58 (m, 24H, tetraethylene glycol chain); $^{13}$C NMR (CDCl$_3$/CD$_3$OD, 0.3 mL/0.2 mL) δ (ppm): 158.2, 136.5, 130.3, 127.6, 127.5, 126.4, 126.2, 114.6, 72.5, 70.55, 70.50, 70.38, 70.02, 69.63, 67.3, 61.2. MS (MALDI): m/z 666.8 [M]$^+$, 667.8 [M+1]$^+$, 689.7 [M+Na]$^+$.

Example 25

This example describes the monotritylation of E,E-1,4-Bis-4,4'-(2-(2-(2-(2-hydroxyethoxy)ethoxy)ethoxy)ethoxy) styryl benzene. E,E-1,4-Bis-4,4'-(2-(2-(2-(2-hydroxyethoxy)ethoxy)ethoxy)ethoxy)styryl benzene (375 mg, 0.56 mmol) was dissolved in dry pyridine (50 mL), followed by addition of DMTrCl (415 mg, 1.23 mmol) and DMAP (~10 mg). The mixture was stirred at room temperature under argon overnight, and TLC monitoring (10/0.75, DCM/MeOH) showed the formation of monosubstituted (Rf 0.32) and disubstituted (Rf 0.74) products as well as the starting material (Rf 0.14). The reaction mixture was concentrated in vacuum and the residue was subject to a silica gel column with CH$_2$Cl$_2$/MeOH/pyridine (100/5/0.5) as eluents affording the title product (160 mg, yield 30%) as a yellow powder. Meanwhile, disubstituted fraction was also collected and further monodetritylation was carried out as the following: A detritylation solution was made by mixing ZnCl$_2$ (1.5 g) into 110 mL of CH$_2$Cl$_2$/MeOH (10/1, v/v). The disubstituted compound (150 mg, 0.12 mmol) was then dissolved in 50 mL of the detritylation solution and the reaction mixture was monitored by TLC (20/1, CH$_2$Cl$_2$/MeOH). Once the appearance of the spot corresponding to starting material (E,E-1,4-Bis-4,4'-(2-(2-(2-(2-hydroxyethoxy)ethoxy)ethoxy)ethoxy)styryl benzene) on the TLC plate, the reaction was quenched by pouring into a saturated aq. NaHCO$_3$ solution. The mixture was extracted by chloroform, and the organic layer was washed with brine, collected, dried over Na$_2$SO$_4$, concentrated, and subject to a silica gel column (100/5/0.5, CH$_2$Cl$_2$/MeOH/pyridine) to give the title product (48 mg, yield 42%). Based on the starting material, the total yield of the monosubstituted product is 38%. The product is stored with a stabilizer (diisopropylethylamine) under argon at −80° C. $^1$H NMR (CDCl$_3$) δ (ppm): 7.46 (s, 4H, aromatic ring of styryl benzene), 7.49–7.38 (m, 6H, aromatic rings of styryl benzene and DMTr), 7.34 (dt, 4H, J$_1$=8.7 Hz, J$_2$=2.3 Hz, methoxylbenzene ring), 7.31–7.15 (m, 3H, benzene ring of DMTr), 7.06 (d, 1H, J=16.2 Hz, double bond trans-linkage), 7.05 (d, 1H, J=16.2 Hz, double bond trans-linkage), 6.96 (d, 1H, J=16.2 Hz, double bond trans-linkage), 6.95 (d, 1H, J=16.2 Hz, double bond trans-linkage), 6.94–6.84 (m, 4H, aromatic ring of styryl benzene), 6.81 (dt, 4H, J$_1$=8.7 Hz, J$_2$=2.3 Hz, methoxylbenzene ring), 4.19–4.08 (m, 4H, tetraethylene glycol chain), 3.89–3.82 (m, 4H, tetraethylene glycol chain), 3.80–3.58 (m, 28H, CH$_3$O and tetraethylene glycol chain), 3.22 (t, 2H, J=5.1 Hz, DMTrOCH$_2$); $^{13}$C NMR (CDCl$_3$) δ (ppm): 158.57, 158.55, 158.43, 145.2, 136.74, 136.70, 136.4, 130.47, 130.40, 130.2, 128.3, 128.00, 127.96, 127.87, 127.79, 126.77, 126.67, 126.44, 126.38, 115.0, 113.2, 86.1, 72.7, 71.09, 71.04, 70.98, 70.95, 70.88, 70.81, 70.56, 69.95, 67.64, 63.4, 62.0, 55.4.

Example 26

This product of ditritylation of E,E-1,4-Bis-4,4'-(2-(2-(2-(2-hydroxyethoxy)ethoxy)ethoxy)ethoxy)styryl benzene had the following characterization data: $^1$H NMR (CDCl$_3$) δ (ppm): 7.46 (s, 4H, aromatic ring of styryl benzene), 7.49–7.39 (m, 4H, aromatic rings of styryl benzene and DMTr), 7.34 (dt, 8H, J$_1$=9.0 Hz, J$_2$=2.7 Hz, methoxylbenzene ring), 7.30–7.15 (m, 3H, aromatic ring of DMTr), 7.05 (d, 2H, J=16.2 Hz, double bond trans-linkage), 6.96 (d, 2H, J=16.2 Hz, double bond trans-linkage), 6.88 (bd, 4H, J=8.7 Hz, aromatic ring of styryl benzene), 6.81 (dt, 8H, J$_1$=9.0 Hz, J$_2$=2.7 Hz, methoxylbenzene ring), 4.12 (bt, 4H, J=4.8 Hz, tetraethylene glycol chain), 3.85 (bt, 4H, J=4.8 Hz, tetraethylene glycol chain), 3.77 (s, 12H, CH$_3$O), 3.78–3.64 (m, 20H, tetraethylene glycol chain), 3.22 (t, 2H, J=5.1 Hz, DMTrOCH$_2$); $^{13}$C NMR (CDCl$_3$) δ (ppm): 158.45, 158.32, 145.1, 136.6, 136.3, 130.2, 130.1, 128.2, 127.87, 127.76, 127.67, 126.66, 126.56, 126.2, 114.8, 113.1, 86.0, 70.95, 70.85, 70.82, 69.8, 67.5, 63.2, 55.3.

Example 27

This example describes the synthesis of the phosphoramidite of monotritylated E,E-1,4-bis-4,4'-(2-(2-(2-(2-hydroxyethoxy)ethoxy)ethoxy)ethoxy)styryl benzene. To a solution of monotritylated E,E-1,4-bis-4,4'-(2-(2-(2-(2-hydroxyethoxy)ethoxy)ethoxy)ethoxy)styryl benzene (86 mg, 0.089 mmol) in 15 mL CH$_2$Cl$_2$ (dry) was added 5 equivalent of diisopropylethylamine (0.08 mL). Then chloro-N,N-diisopropylaminocyanoethoxyphosphane (0.04 mL, 0.18 mmol, ~2 equal) was added dropwise at room temperature under argon. After 20 min of stirring under argon at room temperature, the reaction mixture was diluted with 100 mL of CH$_2$Cl$_2$/Et3N (300/15, v/v), and the organic phase was washed with a saturated aq. NaHCO$_3$ solution and brine. The organic layer was dried over Na$_2$SO$_4$, filtered, and evaporated to dryness. The residue was subject to a silica gel column (CH$_2$Cl$_2$/EtOAc/Et3N, 3/6/1) to give the title product (88 mg, yield 85%) as a yellow powder, which should be used freshly for the next phosphotriester step in order to achieve a higher coupling yield. See, *J. Am. Chem. Soc.*, 125:5248–5249, 2003.

Example 28

This example describes the preparation of a precursor to EE-4-dicyanomethylene-2,6-bis-p-N,N'-n-butyl-N,N'-(2-(2-(2-hydroxyethoxy)ethoxy)ethoxy)ethyl)-aminostyryl pyran: 2-(2-(2-(2-N-n-Butylaminoethoxy)ethoxy)ethoxy) ethanol (ww-70). To a solution of 2-(2-(2-(2-chloroethoxy) ethoxy)ethoxy)ethanol (2 g, 9.4 mmol) in n-butylamine 10 mL at room temperature was added K$_2$CO$_3$ (1 g, 0.77 equal). The reaction mixture was heated to reflux for 24 h. Then another 10 mL of n-butylamine was added into the mixture and the reaction was continued to reflux another 12 hrs. The reaction mixture was cooled to room temperature and the n-butylamine was removed in vacuum. The residue was diluted with CHCl$_3$ and the suspension was suction-filtered. The filtrate was collected and concentrated to give the title product as yellow syrup in quantitative yield, which could be used directly to the next step without further purification. $^1$H NMR (CDCl$_3$) δ (ppm): 3.55–3.51 (m, 14H, tetraethylene glycol chain), 2.66 (bt, 2H, J=5.1 Hz, tetraethylene glycol chain), 2.47 (t, 2H, J=7.2 Hz, n-butyl chain), 1.43–1.31 (m, 2H, n-butyl chain), 1.30–1.16 (m, 2H, n-butyl chain), 0.80 (t, 3H, J=7.2 Hz, n-butyl chain); $^{13}$C NMR (CDCl$_3$) δ (ppm): 72.9, 70.6, 70.4, 70.3, 70.2, 61.3, 49.5, 49.2, 32.1, 20.6, 14.1.

Example 29

This example describes the preparation of 4-N-n-butyl-N-[2-[2-[2-(2-hydroxyethoxy)ethoxy]ethoxy]ethyl]aminobenzaldehyde. A mixture of 2-[2-[2-(2-N-n-butylamino-ethoxy)ethoxy]ethoxy]ethanol (2.3 g, 9.4 mmol), 4-fluorobenzaldehyde (1.0 mL, 9.4 mmol), and $K_2CO_3$ (1.5 g, 1.1 equal) in dry N,N-dimethylformamide (DMF) (10 mL) was heated with stirring to 120° C. (oil bath 128° C.) under argon. The stirring was continued at this temperature for 72 h, and the reaction mixture was cooled to room temperature. After the solvent (DMF) was evaporated in vacuum, the residue was diluted with $CHCl_3$. The obtained suspension was washed with brine (2×200 mL) and dried over $Na_2SO_4$. The organic layer was concentrated and the residue was purified by chromatography on a silica gel column eluted with EtOAc/MeOH (20:1) to give the title product (1.2 g, 36%) as a yellow oil: $R_f$ 0.4 (EtOAc/MeOH 20/1). $^1$H NMR ($CDCl_3$) δ (ppm): 9.56 (s, 1H, —CHO), 7.57 (bd, 2H, J=9.3 Hz, aromatic ring), 6.58 (bd, 2H, J=8.7 Hz, aromatic ring), 3.65–3.40 (m, 16H, tetraethylene glycol chain), 3.29 (t, 2H, J=7.8 Hz, n-butyl chain), 1.59–1.40 (m, 2H, n-butyl chain), 1.30–1.18 (m, 2H, n-butyl chain), 0.85 (t, 3H, J=7.5 Hz, n-butyl chain); $^{13}$C NMR ($CDCl_3$) δ (ppm): 189.7, 152.4, 131.9, 124.5, 110.6, 72.4, 70.5, 70.4, 70.3, 70.1, 68.1, 61.4, 51.1, 50.3, 28.9, 20.0, 13.9.

Example 30

This example describes the synthesis of EE-4-dicyanomethylene-2,6-bis-p-N,N'-n-butyl-N,N'-(2-(2-(2-(2-hydroxyethoxy)ethoxy)ethoxy)ethyl)-aminostyryl pyran. A mixture of 2,6-dimethyl-4-(dicyanomethylene) pyran (220 mg, 1.28 mmol), 4-N-n-butyl-N-[2-[2-[2-(2-hydroxyethoxy)ethoxy]ethoxy]ethyl]aminobenzaldehyde (1.0 g, 2.8 mmol), and piperidine (1 mL, 10 mmol) in toluene (25 mL) was heated to reflux with a Dean-Stark trap under argon overnight. Then the reaction was cooled and the solvent was evaporated to dryness in vacuum. $CHCl_3$ was added to dilute the residue, and the organic layer was washed with water (100 mL) and brine (100 mL). After dried over $Na_2SO_4$, the organic phase was concentrated and the residue was purified by chromatography on a silica gel column eluted with EtOAc/MeOH (20:1) to give the title product (538 mg, yield 50%) as a red powder: $R_f$ 0.14 (EtOAc/MeOH 20/1). $^1$H NMR ($CDCl_3$) δ (ppm): 7.42 (d, 4H, J=9.0 Hz, aromatic ring), 7.41 (d, 2H, J=16.2 Hz, double bond trans-linkage), 6.69 (d, 4H, J=9.0 Hz, aromatic ring), 6.51 (s, 2H, pyran ring), 6.47 (d, 2H, J=16.2 Hz, double bond trans-linkage), 3.55–3.51 (m, 32H, tetraethylene glycol chain), 3.39 (t, 4H, J=7.5 Hz, n-butyl chain), 1.70–1.52 (m, 4H, n-butyl chain), 1.46–1.30 (m, 4H, n-butyl chain), 0.98 (t, 6H, J=7.5 Hz, n-butyl chain); $^{13}$C NMR ($CDCl_3$) δ (ppm): 159.4, 156.2, 149.8, 138.2, 129.9, 122.1, 116.5, 112.8, 111.7, 105.3, 72.6, 70.9, 70.8, 70.7, 70.4, 68.5, 61.8, 51.4, 50.5, 29.4, 20.4, 14.2. MS (MALDI): m/z 844.2 [M+1]$^+$.

Example 31

This example describes the monotritylation of E,E-4-Dicyanomethylene-2,6-bis-p-N,N'-n-butyl-N,N'-(2-(2-(2-(2-hydroxyethoxy)ethoxy)ethoxy)ethyl)-aminostyryl pyran. E,E-4-Dicyanomethylene-2,6-bis-p-N,N'-n-butyl-N,N'-(2-(2-(2-(2-hydroxyethoxy)ethoxy)ethoxy)ethyl)-aminostyryl pyran (538 mg, 0.64 mmol) was dissolved in dry pyridine (50 mL), followed by addition of 3 equivalence of DMTrCl (684 mg) and DMAP (~10 mg). The mixture was stirred at room temperature under argon for 5 days, and TLC monitoring (20/1, DCM/MeOH) showed the formation of mono-substituted (Rf 0.25) and disubstituted (Rf 0.98) products as well as the starting material (Rf 0.09). The reaction mixture was concentrated in vacuum and the residue was directly subject to a silica gel column using the gradient elution technique with $CH_2Cl_2$/MeOH/pyridine (500/10/3 to 500/20/3) as eluents affording the monosubstituted product (250 mg, yield 35%); disubstituted product, and recovered starting material (123 mg). Meanwhile, disubstituted fraction was collected and further monodetritylation was carried out according to the following procedure: A detritylation solution was made by mixing $ZnCl_2$ (1.5 g) with 110 mL of $CH_2Cl_2$/MeOH (10/1, v/v). Then the crude disubstituted compound (~900 mg) was dissolved by 50 mL of the detritylation solution and the reaction mixture was monitored by TLC (20/1, $CH_2Cl_2$/MeOH). Once the appearance of the spot corresponding to the starting matrerial (EE-4-Dicyanomethylene-2,6-bis-p-N,N'-n-butyl-N,N'-(2-(2-(2-(2-hydroxyethoxy)ethoxy)ethoxy)ethyl)-aminostyryl pyran) on the TLC plate, the reaction was quenched by addition of a saturated aq. $NaHCO_3$ solution (100 mL). The mixture was extracted by chloroform, and the organic layer was washed with brine, collected, dried over $Na_2SO_4$, concentrated, and subject to a silica gel column (500/10/3, $CH_2Cl_2$/MeOH/pyridine) to give the title product (128 mg, yield 17.5%). If the recovered starting material was counted, the total yield of the monotritylation would be 67% based on the consumed starting material. $^1$H NMR ($CDCl_3$) δ (ppm): 7.49–7.38 (m, 8H, aromatic rings and double bond trans-linkage), 7.34 (dt, 4H, $J_1$=2.7 Hz, $J_2$=9 Hz, methoxylbenzene ring), 7.31–7.15 (m, 3H, benzene ring), 6.81 (dt, 4H, $J_1$=2.7 Hz, $J_2$=9 Hz, methoxylbenzene ring), 6.69 (d, 2H, J=8.7 Hz, benzene ring), 6.66 (d, 2H, J=9.0 Hz, benzene ring), 6.54 (d, 1H, J=2.1 Hz, pyran ring), 6.52 (d, 1H, J=2.1 Hz, pyran ring), 6.48 (d, 1H, J=15.9 Hz, double bond trans-linkage), 6.46 (d, 1H, J=15.9 Hz, double bond trans-linkage), 3.77 (s, 6H, $CH_3O$), 3.56–3.50 (m, 30H, tetraethylene glycol chain), 3.44–3.31 (m, 4H, n-butyl chain), 3.22 (t, 2H, J=5.1 Hz, tetraethylene glycol chain), 1.69–1.49 (m, 4H, n-butyl chain), 1.48–1.42 (m, 4H, n-butyl chain), 0.97 (t, 3H, J=7.5 Hz, n-butyl chain), 0.96 (t, 3H, J=7.5 Hz, n-butyl chain). $^{13}$C NMR ($CDCl_3$) δ (ppm): 159.5, 158.4, 156.2, 149.8, 145.1, 138.2, 136.4, 130.2, 129.9, 128.3, 127.8, 126.7, 122.2, 122.1, 116.5, 113.1, 112.94, 112.88, 111.8, 111.7, 105.4, 86.1, 72.7, 71.0, 70.92, 70.84, 70.76, 70.5, 68.6, 63.3, 61.9, 56.1, 55.4, 51.4, 50.6, 29.4, 20.5, 14.3. MS (ESI): m/z 1145.6 [M]$^+$.

Example 32

This example describes the synthesis of the phosphoramidite of monotritylated E,E-4-dicyanomethylene-2,6-bis-p-N,N'-n-butyl-N,N'-(2-(2-(2-(2-hydroxyethoxy)ethoxy)ethoxy)ethyl)-aminostyryl pyran. To a solution of monotritylated E,E-4-Dicyanomethylene-2,6-bis-p-N,N'-n-butyl-N,N'-(2-(2-(2-(2-hydroxyethoxy)ethoxy)ethoxy)ethyl)-aminostyryl pyran (200 mg, 0.17 mmol) in dry $CH_2Cl_2$ (20 mL) was added 2.7 equivalent of diisopropyl-ethylamine (0.08 mL). Then chloro-N,N-diisopropylaminocyanoethoxyphosphane (0.05 mL, ~1.2 equal) was added dropwise at room temperature under argon. After 20 min of stirring under argon at room temperature, the reaction mixture was diluted with $CH_2Cl_2$/Et3N (300/15, v/v) 100 mL and the organic phase was washed with a saturated aq. $NaHCO_3$ solution and brine. The organic layer was dried over $Na_2SO_4$, filtered, and evaporated to dryness. The residue was immediately subject to a silica gel column ($CH_2Cl_2$/EtOAc/Et3N, 3/6/1) to give the title product (200 mg, yield 88%) as a red powder, which should be used freshly for the next phosphotriester step in order to achieve a higher coupling yield.

Example 33

This example describes the purification of synthetic foldamers (conjugates of fluorescent chromophores and oligonucleotides) produced in the prior examples using a DNA synthesizer. Typically, using optimized protocols and the Expedite™ 8900 Nucleic Acid Synthesis System, the Oligonucleotide Purification Cartridge (ABI Masterpiece™) is used to purify the obtained crude oligonucleotides with the tail DMTr group on, and typically (depending on the high average coupling yield (>99%) during chain assembly) the conjugates of fluorescent chromophores and oligonucleotides purified in this fashion can be introduced directly on our DNA detection study after being desalted.

Once the synthesis was complete, the column (0.2 μmol scale) with the designed oligomer was removed from the DNA synthesizer. With the plunger fully depressed into the barrel, a slip-tip luer syringe was attached to one end of the column. 1 mL of fresh NH$_4$OH was drawn into a second luer tip syringe that was attached to the other end of the column. The syringe plunger was depressed to force the solution back and forth over the support in the column. This procedure was repeated three or four times to ensure that the support in the column was fully saturated, and then the column/syringe assembly was allowed to sit at room temperature for 1 h, after which, the solution was agitated by depressing the syringe plunger three times and the assembly was allowed to rest for another 1 h. The solution was drawn into one of the syringes, and was carefully removed from the column into a 10-mL flask with a sealed septum and a stirring bar. The solution was sealed in the flask and proceeded at room temperature for 48 h. 20 μL of the above sealed solution was diluted with 3000 μL water, and the ODU was measured using UV-Vis. Based on the ODU value, the original concentrated ammonia solution could be diluted (below 10 ODU) for the OPC purification according to the purification protocol provided by ABI Masterpiece™ (2 mL diluted solution for each OPC). The OPC purified trityl-off foldamer were stored as a dry solid at −80° C. According to the desalting protocol provided by ABI Masterpiece™, the trityl-off foldamers were dissolved in water (1 mL), and passed the solution through an activated OPC column, then collected with 1 mL of 50% acetonitrile-water solution. The obtained acetonitrile-water solution was then concentrated to dryness in vacuum and the salt-free foldamer was obtained as a solid, which could be stored at −20° C. for the further study.

It will be apparent to those of ordinary skill in the art that various modifications and variations can be made in the present compounds, compositions and methods without departing from the scope or spirit of the disclosure. Other embodiments of the compounds, compositions and methods will be apparent to those skilled in the art from consideration of the specification and practice of the procedures disclosed herein. It is intended that the specification and examples be considered as exemplary only, with a true scope and spirit of the invention being indicated by the following claims.

We claim:

1. A probe, comprising:
   n chromophore moieties; and
   from (n−1) to (n+1) flexible linker moieties linking the chromophore moieties, wherein n is at least 3 and at least one flexible linker moiety selectively binds to a target molecule.

2. The probe according to claim 1, wherein at least one flexible linker comprises a nucleic acid sequence.

3. The probe according to claim 1, wherein at least one flexible linker selectively binds to a protein.

4. The probe according to claim 3, wherein the protein is a transcription factor.

5. The probe according to claim 2, wherein the nucleic acid sequence comprises an AT-rich region, an AP-1 site, a NF-κB site, or a combination thereof.

6. The probe according to claim 3, wherein the protein is HMGA1, HMGB, NF-κB, c-Fos, or c-Jun.

7. The probe according to claim 1, wherein at least one chromophore moiety fluoresces when at least one chromophore moiety is stimulated.

8. The probe according to claim 1, wherein the chromophore moieties are the same.

9. The probe according to claim 1, wherein the chromophore moieties are selected from the group consisting of perylene tetracarboxylic diimide, oligophenylenevinylene (OPV), 2,6-diaminostyryl 4-dicyanomethylene-4H-pyran or DAP, derivatives thereof, and combinations thereof.

10. The probe according to claim 1, wherein the chromophore moieties comprise at least one FRET pair.

11. The probe according to claim 9, wherein the FRET pair includes a DAP-1 chromophore moiety and an OPV-1 moiety.

12. The probe according to claim 1, wherein the wavelength of an absorption or emission maximum of at least one chromophore moiety shifts when the linker binds to the target molecule.

13. The probe according to claim 1, wherein the chromophores reversibly non-covalently associate in the absence of the target molecule and dissociate upon target molecule binding.

14. The probe according to claim 13, wherein the chromophores non-covalently associate via stacking.

15. The probe according to claim 1, wherein n=3 to 10.

16. The probe according to claim 1, wherein at least a first and a second chromophore moiety are different.

17. The probe according to claim 16, wherein a light emission of the first chromophore moiety overlaps with a light absorption wavelength band of the second chromophore moiety.

18. The probe according to claim 17, further comprising a third chromophore moiety having an absorption-light overlapping with a light emission of the second chromophore moiety.

19. The probe according to claim 1, wherein the n chromophore moieties are linked to and from (n−1) to (n+1) DNA oligonucleotides, and wherein a DNA oligonucleotide is positioned between each chromophore.

20. The probe according to claim 19, wherein the chromophore moieties are covalently linked to the DNA oligonucleotides by means of polyalkylene oxide groups.

21. The probe according to claim 20, wherein the polyalkylene oxide groups are tetraethylene glycol moieties.

22. The probe according to claim 1, wherein the probe has a first end and a second end.

23. The probe according to claim 1, wherein the probe is cyclic.

24. The probe according to claim 1, wherein the probe has or adopts a folded structure at an elevated temperature, wherein the elevated temperature is from about 25° C. to about 90° C.

25. The probe according to claim 24, wherein the probe comprises plural perylene moieties.

26. The probe according to claim 24, wherein the probe unfolds upon binding to the target biomolecule to give an unfolded structure.

27. The probe according to claim 26, wherein the unfolded structure exhibits a spectrum distinct from the folded structure.

28. A kit for identifying or indicating the presence of a biomolecule, comprising the probe of claim 1.

29. The kit according to claim 28, further comprising instructions.

30. A probe, comprising:
a plurality of interacting chromophore moieties;
one or more flexible linker moieties linking the chromophore moieties, wherein at least one of the linker moieties is not a nucleic acid sequence; and
at least one group that selectively binds to a target molecule.

31. The probe according to claim 30, wherein one or more of the flexible linkers comprises a nucleic acid sequence.

32. The probe according to claim 30, wherein at least one flexible linker selectively binds to a biomolecule.

33. The probe according to claim 30, wherein the chromophore moieties comprise at least one FRET pair.

34. The probe according to claim 30, wherein the wavelength of an absorption or emission maximum of at least one chromophore moiety shifts when the linker binds to the target molecule.

35. The probe according to claim 30, wherein the chromophores reversibly non-covalently associate in the absence of the target molecule and dissociate upon target molecule binding.

36. The probe according to claim 30, wherein the probe comprises n chromophore moieties and from (n−1) to (n+1) flexible linker moieties, wherein at least one flexible linker moiety selectively binds to a target molecule.

37. The probe according to claim 36, wherein n=2 to 10.

38. The probe according to claim 36, wherein n is at least 3.

39. The probe according to claim 38, wherein at least a first and a second chromophore moiety are different.

40. The probe according to claim 28, further comprising a third chromophore moiety having an absorption-light overlapping with a light emission of the second chromophore moiety.

41. The probe according to claim 31, wherein the chromophore moieties are covalently linked to the nucleic acid sequence by means of polyalkylene oxide groups.

42. The probe according to claim 41, wherein the polyalkylene oxide groups are tetraethylene glycol moieties.

43. The probe according to claim 30, wherein the probe has a first end and a second end.

44. The probe according to claim 30, wherein the probe is cyclic.

45. A probe, comprising:
plural interacting chromophore moieties; and
at least one flexible linker moiety linking the chromophore moieties; and
at least one group that selectively binds a target molecule, wherein the wavelength of an absorption or emission maximum of at least one chromophore moiety shifts when the group binds to the target molecule.

46. The probe according to claim 45, wherein at least one flexible linker comprises a nucleic acid sequence.

47. The probe according to claim 45, wherein at least one flexible linker selectively binds to a biomolecule.

48. The probe according to claim 45, wherein the chromophore moieties are the same.

49. The probe according to claim 45, wherein the chromophore moieties comprise at least one FRET pair.

50. The probe according to claim 45, wherein the probe comprises n chromophore moieties and from (n−1) to (n+1) flexible linker moieties, wherein at least one flexible linker moiety selectively binds to a target molecule.

51. The probe according to claim 50, wherein n=2 to 10.

52. The probe according to claim 50, wherein n is at least 3.

53. The probe according to claim 52, wherein at least a first and a second chromophore moiety are different.

54. The probe according to claim 50, wherein the n chromophore moieties are linked to and from (n−1) to (n+1) DNA oligonucleotides, and wherein a DNA oligonucleotide is positioned between each chromophore.

55. The probe according to claim 54, wherein the chromophore moieties are covalently linked to the DNA oligonucleotides by means of polyalkylene oxide groups.

56. The probe according to claim 45, wherein the probe has a first end and a second end.

57. The probe according to claim 45, wherein the probe is cyclic.

* * * * *